United States Patent [19]

Durvasula et al.

[11] Patent Number: 5,300,594
[45] Date of Patent: Apr. 5, 1994

[54] BIS(AMINOPHENOXY)-ALPHA-SUBSTITUTED STILBENES, CURABLE MIXTURES WITH EPOXY RESINS AND CURED PRODUCTS

[75] Inventors: V. Rao Durvasula; Robert E. Hefner, Jr.; Jimmy D. Earls, all of Lake Jackson, Tex.

[73] Assignee: The Dow Chemical Company, Midland, Mich.

[21] Appl. No.: 58,100

[22] Filed: May 6, 1993

[51] Int. Cl.$^5$ .................... C08G 59/00; C08G 65/08; C08G 65/14
[52] U.S. Cl. .................... 525/502; 525/529; 528/98; 528/97; 526/273
[58] Field of Search .................... 528/98, 97; 525/502, 525/529; 526/273

[56] References Cited

U.S. PATENT DOCUMENTS

| | | | |
|---|---|---|---|
| 4,517,321 | 5/1985 | Gardner et al. | 528/124 |
| 4,579,885 | 4/1986 | Domeier et al. | 528/124 |
| 4,608,404 | 8/1986 | Gardner et al. | 523/400 |
| 4,645,803 | 2/1987 | Kohli et al. | 528/98 |
| 4,661,559 | 4/1987 | Gardner et al. | 525/65 |
| 4,721,799 | 1/1988 | Newmann-Evans | 549/552 |
| 4,746,718 | 5/1988 | Gardner et al. | 525/471 |
| 4,760,106 | 7/1988 | Gardner et al. | 523/433 |
| 4,891,408 | 1/1990 | Newmann-Evans | 525/113 |
| 4,916,202 | 4/1990 | Butler et al. | 528/99 |

OTHER PUBLICATIONS

Derwent Abstract 87-040949/06.
Derwent Abstract 86-227040/35.
Derwent Abstract 85-013574/04.
Derwent Abstract 84-295910/48.
Derwent Abstract 78-71359A/40(71359A).
Derwent Abstract 92-163731/20.
Derwent Abstract 92-127177/16.
Derwent Abstract 90-155141/20.
Derwent Abstract 88-310764/44.
Derwent Abstract 87-279208/40.
Derwent Abstract 87-195178/28.
Chemical Abstracts 111(4):24493z.
Chemical Abstracts 110(12):96561x.
Chemical Abstracts 108(6):39088h.
Chemical Abstracts 107(26):238043u.
Chemical Abstracts 107(18):155397m.
Chemical Abstracts 105(23):208599w.
Chemical Abstracts 117(17):170496t.
Chemical Abstracts 117(15):150694c.
Chemical Abstracts 117(6):51294r.
Chemical Abstracts 116(16):153028d.
Chemical Abstracts 113(10):79849s.
Chemical Abstracts 112(10):78590t.

*Primary Examiner*—Frederick Krass

[57] ABSTRACT bis(Aminophenoxy)-alpha-substituted stilbenes are prepared by reacting a dihydroxy-alpha-substituted stilbene with a halonitrobenzene in the presence of a basic acting substance such as potassium carbonate and hydrogenating the resulting bis(nitrophenoxy)-alpha-substituted stilbene to convert the nitro groups to amino groups. These compounds are useful as curing agents for epoxy resins.

12 Claims, No Drawings

BIS(AMINOPHENOXY)-ALPHA-SUBSTITUTED STILBENES, CURABLE MIXTURES WITH EPOXY RESINS AND CURED PRODUCTS

FIELD OF THE INVENTION

The present invention concerns bis(aminophenoxy)-alpha-substituted stilbenes, curable (thermosettable) mixtures thereof with one or more epoxy resins, as well as the cured (thermoset) compositions thereof.

BACKGROUND OF THE INVENTION

The present invention provides novel bis(aminophenoxy)-alpha-substituted stilbenes which are useful for curing epoxy resins. Epoxy resins are well established as a class of curable compositions which find efficacy in a myriad of applications. The curing of epoxy resins is effected by a wide range of curing agents including, for example, the primary and secondary aliphatic, cycloaliphatic and aromatic polyamines; dicarboxylic acids and the anhydrides thereof; aromatic hydroxyl containing compounds; imidazoles; guanidines; ureaaldehyde resins and alkoxylated derivatives thereof; melamine-aldehyde resins and alkoxylated derivatives thereof; amidoamines; epoxy resin adducts; and various combinations thereof. In many of the applications served by epoxy resins, it would be desirable to improve one or more of the physical and / or mechanical and / or thermal properties of the cured products thereof. The bis(aminophenoxy)-alpha-substituted stilbenes of the present invention are also of useful for preparation of other thermoset polymers, such as, for example, polyurethanes and polyureas.

The bis(aminophenoxy)-alpha-substituted stilbenes of the present invention possess a unique molecular structure heretofore unavailable in an epoxy resin curing agent. One of the features of the molecular structure inherent to the bis(aminophenoxy)-alpha-substituted stilbenes of the present invention is the alpha-substituted stilbene moiety which is a mesogen, especially when 4,4'-disubstitution predominates. A second feature of the molecular structure inherent to the bis(aminophenoxy)-alpha-substituted stilbenes of the present invention is the presence of an ether linkage between each aromatic ring of the alpha-substituted stilbene moiety and each aromatic ring of the aminoaryl group. These ether linkages provide flexibility, thus decoupling the aromatic rings possessing the amino groups from the mesogenic moiety (alpha-substituted stilbene). A third feature of the molecular structure inherent to the bis(aminophenoxy)-alpha-substituted stilbenes of the present invention is the presence of the amino groups on the aromatic rings which are decoupled from the mesogenic moiety via the ether linkages, such that the amino group may be present at any position on the decoupled aromatic ring. Variation of the amino group substitution on the aromatic rings leads to a high degree of control over the type of liquid crystallinity achievable in certain of the curable compositions prepared therefrom and, surprisingly, liquid crystallinity can still be achieved even with ortho substitution by the amino group. The combination of molecular structures inherent to the bis(aminophenoxy)-alpha-substituted stilbenes of the present invention provides curable epoxy resin compositions with outstanding processability and cured epoxy resin compositions thereof with substantial improvements in one or more physical and / or mechanical and / or thermal properties.

SUMMARY OF THE INVENTION

One aspect of the present invention pertains to bis-(aminophenoxy)-alpha-substituted stilbenes represented by the following Formula I

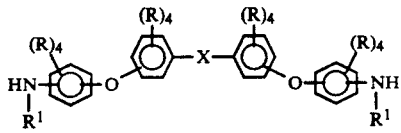

wherein each R Ia Independently hydrogen or a hydrocarbyl or hydrocarbyloxy group having from one to about 10, preferably one to about 4, carbon atoms, a halogen atom, preferably chlorine, bromine or fluorine, a nitro group, a nitrile group or a $-CO-R^2$ group; each $R^1$ is independently hydrogen or a hydrocarbyl group having from one to about 10, preferably one to about 6, carbon atoms; X is a

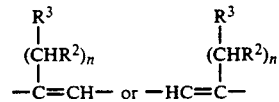

group, each $R^2$ is independently hydrogen or a hydrocarbyl group having from one to about 10, preferably one to about 2, carbon atoms; $R^3$ is a hydrocarbyl group having from one to about 10, preferably one to about 2, carbon atoms and may be chlorine or a nitrile group, when n has a value of zero; and n has a value of zero or one.

Another aspect of the present invention pertains to curable (thermosettable) compositions comprising (A) a curing amount of one or more bis(aminophenoxy)-alpha-substituted stilbenes and (B) one or more epoxy resins.

A further aspect of the present invention pertains to curable compositions which have been subjected to the application of an electric field or magnetic field or drawing and/or shear flow before and/or during curing or processing of the aforesaid curable compositions and wherein said bis(aminophenoxy)-alpha-substituted stilbene is mesogenic.

A further aspect of the present invention pertains to products resulting from curing the aforementioned curable compositions.

A still further aspect of the present invention pertains to a process for preparing bis(aminophenoxy)-alpha-substituted stilbenes which comprises (1) reacting a dihydroxy-alpha-substituted stilbene with a halonitrobenzene in the presence of a basic acting substance; followed by (2) hydrogenating the resultant bis(nitrophenoxy)-alpha-substituted stilbene to convert the nitro groups to amino groups and thereafter recovering the thus prepared bis(aminophenoxy)-alpha-substituted stilbene.

DETAILED DESCRIPTION OF THE INVENTION

DEFINITIONS

The term "hydrocarbyl" as employed herein means any aliphatic, cycloaliphatic, aromatic, aryl substituted aliphatic or cycloaliphatic or aliphatic or cycloaliphatic substituted aromatic groups. The aliphatic or cycloaliphatic groups can be saturated or unsaturated. Likewise, the term "hydrocarbyloxy" means a hydrocarbyl group having an oxygen linkage between it and the carbon atom to which it is attached.

The term "mesogenic" or "mesogen" as is used herein designates compounds containing one or more rigid rodlike structural units which have been found to favor the formation of liquid crystal phases in the case of low molar mass substances. Thus the mesogen or mesogenic moiety is that structure responsible for molecular ordering. The term mesogenic is further defined by R. A. Weiss (ed.) and C. K. Ober (ed.) in *Liquid-Crystalline Polymers*, ACS Symposium Series 435 (1989) on pages 1-2: "The rigid unit responsible for the liquid crystalline behavior is referred to as the mesogen," and "Liquid crystalline order is a consequence solely of molecular shape anisotropy, such as found in rigid rod-shaped molecules. . ." and "Liquid crystal is a term that is now commonly used to describe materials that exhibit partially ordered fluid phases that are intermediate between the three dimensionally ordered crystalline state and the disordered or isotropic fluid state. Phases with positional and/or orientational long-range order in one or two dimensions are termed mesophases. As a consequence of the molecular order, liquid crystal phases are anisotropic, i.e., their properties are a function of direction." Further definition of the term mesogenic may be found in *Polymeric Liquid Crystals*, Alexandre Blumstein (ed.), (1983) on pages 2-3: "Compounds forming small molecule thermotropic liquid crystals usually have the following molecular structural features: - high length:breadth (axial) ratio - rigid units such as 1,4-phenylene, 1,4-bicyclooctyl, 1,4-cyclohexyl, etc., - rigid central linkages between rings such as —COO—, —CH=CH—, —N=NO—, —N=N—, etc. - anisotropic molecular polarization".

The terms "curable" and "thermosettable" are used synonamously throughout and mean that the composition is capable of being subjected to conditions which will render the composition to a cured or thermoset state or condition.

The terms "cured" and "thermoset" are used synonamously throughout. The term "thermoset" is defined by L. R. Whittington in *Whittington's Dictionary of Plastics* (1968) on page 239: "Resin or plastics compounds which in their final state as finished articles are substantially infusible and insoluble. Thermosetting resins are often liquid at some stage in their manufacture or processing, which are cured by heat, catalysis, or some other chemical means. After being fully cured, thermosets cannot be resoftened by heat. Some plastics which are normally thermoplastic can be made thermosetting by means of crosslinking with other materials."

BIS(AMINOPHENOXY)-ALPHA-SUBSTITUTED STILBENE PREPARATION

The bis(aminophenoxy)-alpha-substituted stilbenes of the present invention can be prepared by reacting the corresponding dihydroxy-alpha-substituted stilbene compound with a halonitrobenzene in the presence of a basic acting substance and, optionally, one or more solvents, to provide the corresponding bis(nitrophenoxy)-alpha-substituted stilbene. The resultant bis(nitrophenoxy)-alpha-substituted stilbene is then hydrogenated to selectively convert the nitro groups to amine groups.

Suitable dihydroxy-alpha-substituted stilbene compounds which can be employed herein include those represented by the following Formula II

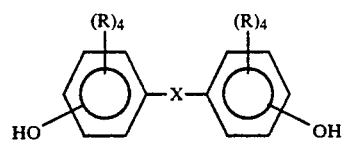

Formula II wherein R, $R^2$, X and n are as hereinbefore defined.

Particularly suitable dihydroxy-alpha-substituted stilbene compounds represented by Formula II which can be employed herein to prepare the bis(nitrophenoxy)-alpha-substituted stilbene precursors to the bis(aminophenoxy)-alpha-substituted stilbene compositions of the present invention include, for example, 4,4'-dihydroxy-alpha-methylstilbene, 4,4'-dihydroxy-alpha-ethylstilbene, 4,4'-dihydroxy-alpha-propylstilbene, 3,3'-dimethyl-4,4'-dihydroxy-alpha-methylstilbene, 3,3',5,5'-tetramethyl-4,4'-dihydroxy-alpha-methylstilbene, 2,2'-dihydroxy-alpha-methylstilbene, 2,4'-dihydroxy-alpha-methylstilbene, 2',4-dihydroxy-alpha-methylstilbene, 4,4'-dihydroxy-alpha-chlorostilbene, 4,4'-dihydroxy-alpha-cyanostilbene, 3,3'-dicyano-4,4'-dihydroxy-alpha-methylstilbene, 3,3'-dichloro-4,4'-dihydroxy-alpha-methylstilbene, 3,3'-dibromo-4,4'-dihydroxy-alpha-methylstilbene, 3,3'-difluoro-4,4'-dihydroxy-alpha-methylstilbene, or any combination thereof and the like.

Halonitrobenzenes suitable for use herein contain the halogen atom ortho or para to a nitro group and include, for example, 2-chloronitrobenzene, 4-chloronitrobenzene, 2-bromonitrobenzene, 4-bromonitrobenzene, 3-methyl-4-chloronitrobenzene, 2-methyl-4-chloronitrobenzene, 3,5-dimethyl-4-chloronitrobenzene, 2,6-dimethyl-4-chloronitrobenzene, 3,6-dimethyl-4-chloronitrobenzene, 2,5-dimethyl-4-chloronitrobenzene, 3-methyl-2-chloronitrobenzene, 3,6-dimethyl-2-chloronitrobenzene, 6-methyl-2-chloronitrobenzene, 2-phenyl-4-chloronitrobenzene, 4-phenyl-2-chloronitrobenzene, or any combination thereof and the like. The halonitrobenzene is usually employed in amounts which provide from about 1.05:1 to about 5:1, more suitably from about 1.10:1 to about 2:1, more suitably from about 1.20:1 to about 1.5:1 equivalents of halonitrobenzene per phenolic hydroxyl group. At amounts of halonitrobenzene below about 1.05 equivalents per phenolic hydroxyl group, conversion of the dihydroxy-alpha-substituted stilbene to the corresponding bis(aminophenoxy)-alpha-substituted stilbene is incomplete or occurs at an undesireably slow rate. Amounts of halonitrobenzene above about 5 equivalents per phenolic hydroxyl group provide an excess dilution of the reaction.

Suitable basic acting substances for use herein to induce formation of the bis(phenolate) of the dihydroxy-alpha-substituted stilbene compounds include, for example, the alkali metal or alkaline earth metal hydroxides, carbonates or any combination thereof and the like, such as sodium hydroxide, potassium hydroxide, lithium hydroxide, calcium hydroxide, barium hydroxide, magnesium hydroxide, manganese hydroxide, sodium carbonate, potassium carbonate, lithium carbonate, calcium carbonate, barium carbonate, magnesium carbonate, manganese carbonate, any combination thereof and the like. Most preferred as the basic acting substance is potassium carbonate. The basic acting substance is usually employed in amounts which provide from about 1.05:1 to about 2:1, more suitably from about 1.10:1 to about 1.5:1, more suitably from about 1.15:1 to about 1.3:1 equivalents of basic acting substance per phenolic hydroxy group. At amounts of basic acting substance below about 1.05 equivalents per phenolic hydroxyl group, conversion of the dihydroxy-alpha-substituted stilbene to the corresponding bis(aminophenoxy)-alpha-substituted stilbene is incomplete or occurs at an undesireably slow rate. Amounts of basic acting substance above about 2 equivalents per phenolic hydroxyl group provide an excess dilution of the reaction.

Suitable solvents which can be employed herein include, for example, an excess of one or more halonitrobenzenes, aliphatic hydrocarbons, aromatic hydrocarbons, glycol ethers, amides, sulfoxides, sulfones, ethers, mixtures thereof and the like. Particularly suitable solvents include, for example, 2,5-dimethylheptane, 4-ethylheptane, 2-methyloctane, nonane, decane, toluene, xylene, decahydronaphthalene, ethylene glycol ethyl ether, ethylene glycol n-butyl ether, ethylene glycol phenyl ether, propylene glycol ethyl ether, propylene glycol n-butyl ether, propylene glycol phenyl ether, diethylene glycol methyl ether, diethylene glycol ethyl ether, diethylene glycol n-butyl ether, diethylene glycol phenyl ether, tripropylene glycol methyl ether, butylene glycol methyl ether, N,N-dimethylformamide, N-methylpyrrolidinone, N,N-dimethylacetamide, dimethylsulfoxide, sulfolane, di-n-butyl ether, diphenyl ether, 2,5-dimethyl-1,4-dioxane, mixtures thereof and the like. Most preferred as the solvent is N,N-dimethylformamide. The solvent is usually employed in amounts of suitably from zero to about 95, more suitably from about 10 to about 80, more suitably from about 20 to about 70, percent by weight based on the combined weight of solvent and reactants. Larger amounts of solvent provide an excess dilution of the reaction.

The reaction to form the bis(nitrophenoxy)-alpha-substituted stilbene precursor to the bis(aminophenoxy)-alpha-substituted stilbene compositions of the present invention can be conducted at atmospheric, superatmospheric or subatmospheric pressures at temperatures of from about 80 deg. C. to about 175 deg. C., preferably from about 100 deg. C. to about 160 deg. C., more preferably from about 125 deg. C. to about 150deg C. The time required to complete the reaction depends upon the temperature, reactants and solvent, if any, employed. Higher temperatures require shorter periods of time whereas longer temperatures require longer periods of time. Generally, however, times of from about thirty minutes to about 96 hours, preferably from about one hour to about 24 hours, more preferably from about 3 hours to about 12 hours are suitable. At temperatures below about 80 deg. C. conversion of the dihydroxy-alpha-substituted stilbene to the corresponding bis(aminophenoxy)-alpha-substituted stilbene is incomplete or occurs at an undesireably slow rate. At temperatures above about 175 deg. C. excessive discoloration or even decomposition of the product occurs.

The resultant bis(nitrophenoxy)-alpha-substituted stilbene precursor to the bis(aminophenoxy)-alpha-substituted stilbene is hydrogenated using methods well known to the skilled artisan. Thus suitable such methods for the reduction of nitro compounds to amines are disclosed by March in *Advanced Organic Chemistry*. John Wiley and Sons, pages 1103 to 1106 (1985). The general methods cited therein for the reduction reaction include the use of iron, zinc or tin plus a mineral acid, catalytic hydrogenation, for example in the presence of platinum, $AlH_3$-$AlCl_3$, hydrazine plus catalyst, dodecacarbonyltriironmethanol, $TiCl_3$, hot liquid paraffin, formic acid and palladium on carbon, sulfides such as NaHS, and sodium dihydro(trithio)borate. For the reduction of the nitro group in the presence of the unsaturated alpha-substituted stilbene moiety, a functional group also susceptible to reduction, certain of the reduction chemistries are preferred. Thus, catalytic reduction using Raney nickel, aqueous ferrous sulfate heptahydrate and ammonium hydroxide, aqueous sodium hydrosulfite and potassium carbonate solution, or powdered zinc in ammonium hydroxide are preferred. Details concerning the three latter aforementioned reduction methods are provided in U.S. Pat. Nos. 3,845,018 and 3,975,444, both of which are incorporated herein by reference in their entirety.

The reduction using catalytic Raney nickel is usually conducted in an inert solvent at superatmospheric hydrogen pressures at a temperature of from about 10 deg. C. to about 150 deg. C., preferably from about 20 deg. C. to about 50 deg. C. The time required to complete the reaction depends upon the temperature, the specific bis(nitrophenoxy)-alpha-substituted stilbene reactant, the amount of catalyst and the solvent employed. Higher temperatures require shorter periods of time whereas longer temperatures require longer periods of time. Generally, however, times of from about 5 minutes to about 24 hours, preferably from about 15 minutes to about 12 hours are suitable. Solvents which can be employed in the hydrogenation include aliphatic alcohols, such as, for example, methanol, ethanol, isopropanol; aliphatic carboxylic acid esters, such as, for example, ethyl acetate; aliphatic or cycloaliphatic ethers and diethers, such as, for example, diethylether, 1,4-dioxane, 2,5-dimethyl-1,4-dioxane; mixtures thereof and the like.

When chemistry to incorporate certain aryl substituents into the bis(aminophenoxy)-alpha-substituted stilbene compositions (Formula I where at least one R is other than hydrogen) is to be practiced, it is frequently of value to protect the amine functionalities prior to the substitution reaction followed by deprotection to regenerate the free amine groups. General methodology for the protection-deprotection of the amine group is well established, for example, as reported by T. W. Greene and P. G. M. Wuts in *Protective Groups in Organic Synthesis* published by John Wiley and Sons, Inc., New York (1991) on pages 309-405. One of the methods cited therein is protection-deprotection of the amine group via formation of the carbamate group. As a specific example of this method, the amine group is protected via reaction with methyl chloroformate at reflux for 12 hours in the presence of potassium carbonate as the hydrochloric acid acceptor. Deprotection (cleavage to the amine group) is accomplished via reaction of the carbamate group with potassium hydroxide, water, ethylene glycol at 100 deg. C. for 12 hours, or by reaction of the carbamate group with hydrobromic acid, acetic acid at 25 deg. C. for 18 hours, or by the reaction of the carbamate group with lithium n-propyl mercaptide at 0 deg. C. for 8.5 hours. A second method cited in the Greene and Wuts reference is protection-deprotection of the amine group via formation of the amide group. As a specific example of this method, the amine group is protected via reaction with trifluoroacetic acid ethyl ester, triethylamine, methanol at 25 deg.

C. for 15 to 45 hours. Deprotection is accomplished via reaction of the trifluoroacetamide group with potassium carbonate, methanol, water at 25 deg. C. or by reaction of the trifluoroacetamide group with ammonia in methanol or by the reaction of the trifluoroacetamide group with 0.2N barium hydroxide in methanol at 25 deg. C. for 2 hours. A third example cited in the Greene and Wuts reference is protection-deprotection of the amine group via formation of the imine group. As a specific example of this method, the amine group is protected via reaction with benzaldehyde in benzene at 25 deg. C. in the presence of sodium sulfate present as the dessicant. Deprotection is accomplished via reaction of the N-benzylideneamine group with 1N hydrochloric acid at 25 deg. C. for one hour or by the reaction of the N-benzylideneamine group with hydrazine in ethanol at reflux for 6 hours. Protection-deprotection is usually desireable only if aryl substitutent(s) are present in the corresponding dihydroxy-alpha-substituted stilbene precursor (Formula II where at least one R is other than hydrogen) which would not survive the aforementioned conditions required for the reactions leading to the bis(aminophenoxy)-alpha-substituted stilbene compositions of the present invention and which cannot themselves be protected then deprotected.

Methods for use in preparing N-substituted bis-(aminophenoxy)-alpha-substituted stilbene compositions (Formula I where at least one $R^1$ is other than hydrogen) can be adapted from the techniques given by Sandler and Karo in *Organic Functional Group Preparations* published by Academic Press, Inc., New York (1983) on pages 387–390. In the general method, the bis(aminophenoxy)-alpha-substituted stilbene is converted to the corresponding bis(acetamidophenoxy)-alpha-substituted stilbene followed by N-alkylation to provide the corresponding N,N'-dialkyl-bis(acetamidophenoxy)-alpha-substituted stilbene. Hydrolytic cleavage of the acetamido group provides the desired N,N'-dialkyl-bis(aminophenoxy)-alpha-substituted stilbene. An additional method for use in preparing the N-substituted bis(aminophenoxy)-alpha-substituted stilbene compositions may be adapted from the technique given by Allen and VanAllan in *Organic Synthesis Collective Volume III* (E. C. Horning (ed.)) published by John Wiley and Sons, Inc., New York (1965 printing on pages 827–828. In the general method, the bis(aminophenoxy)-alpha-substituted stilbene is reacted with a primary alkylaldehyde (cycloaliphatic aldehyde, benzaldehyde) to provide the corresponding imino compound. Hydrogenation, for example using hydrogen with Raney nickel catalyst, of the imino compound provides the desired N,N'-dialkyl-bis(aminophenoxy)-alpha-substituted stilbene.

EPOXY RESINS

The epoxy resins which can be employed to prepare the curable compositions of the present invention include essentially any epoxy-containing compound which contains an average of more than one vicinal epoxide group per molecule. The epoxide groups can be attached to any oxygen, sulfur or nitrogen atom or the single bonded oxygen atom attached to the carbon atom of a —CO—O— group in which said oxygen, sulfur or nitrogen atom or the carbon atom of the —CO—O— group is attached to an aliphatic, cycloaliphatic, polycycloaliphatic or aromatic hydrocarbon group which hydrocarbon group can be substituted with any inert substituent including, but not limited to, halogen atoms, preferably fluorine, bromine or chlorine, nitro groups, and the like or such groups can be attached to the terminal carbon atoms of a compound containing an average of more than one —(O—CHR$^a$—CHR$^a$)$_t$— group where each R$^a$ is independently hydrogen or an alkyl or haloalkyl group, containing from one to about 2 carbon atoms, with the proviso that only one R$^a$ group can be a haloalkyl group, and t has a value from one to about 100, preferably from one to about 20, more preferably from one to about 10, most preferably from one to about 5.

Suitable such epoxy resins which can be combined with the bis(aminophenoxy)-alpha-substituted stilbene compositions to prepare the curable compositions of the present invention include, for example, the glycidyl ethers or glycidyl amines represented by the following Formulas III, IV, V, VI. VII, VIII, IX, X or XI

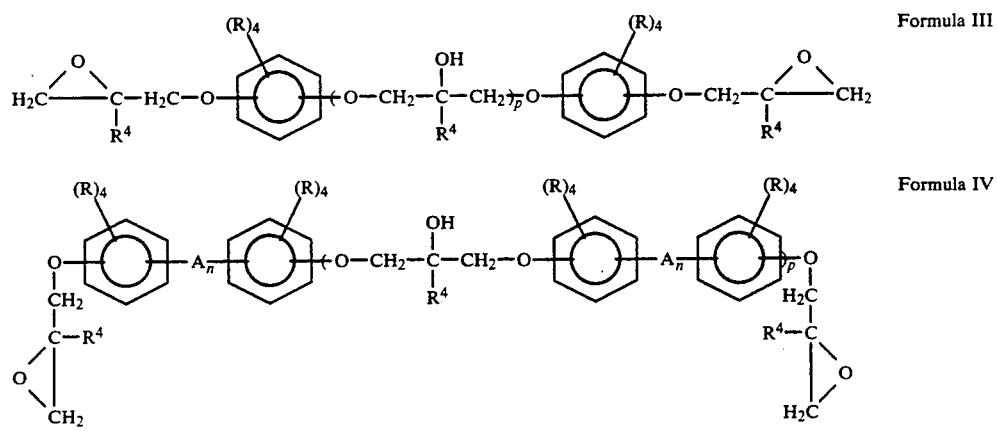

Formula III

Formula IV

-continued
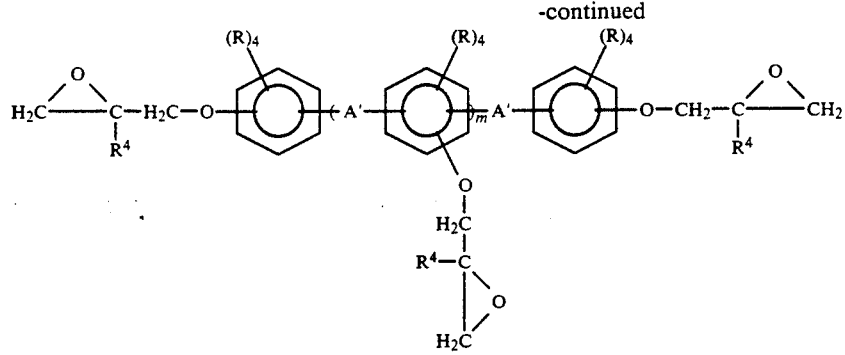
Formula V
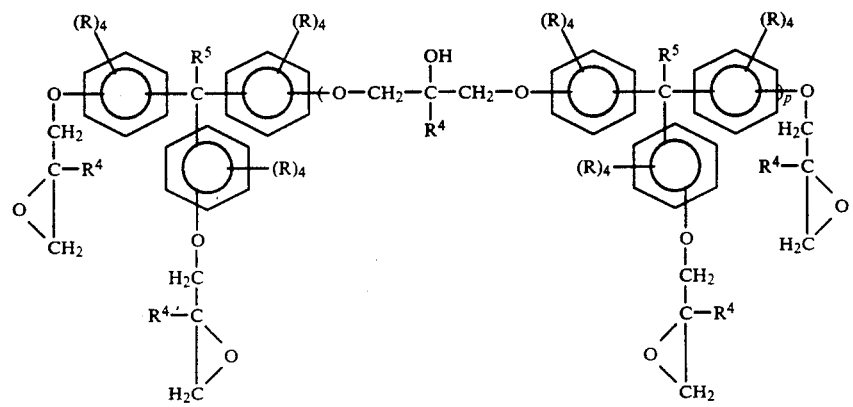
Formula VI
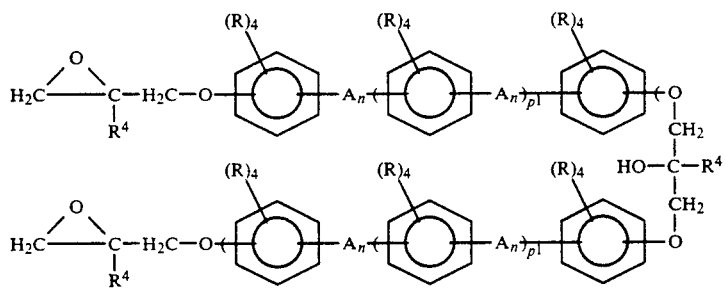
Formula VII
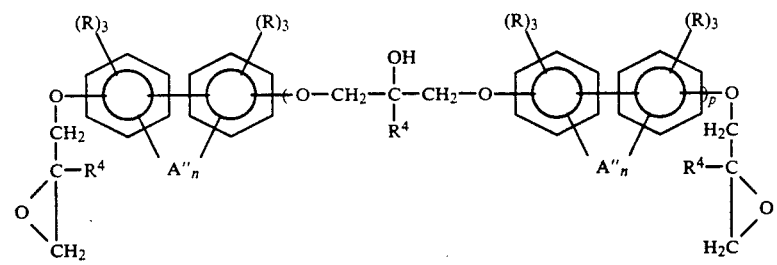
Formula VIII
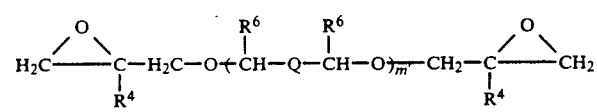
Formula IX
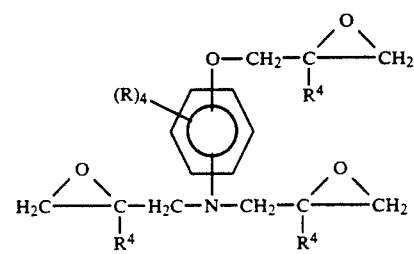
Formula X Formula XI

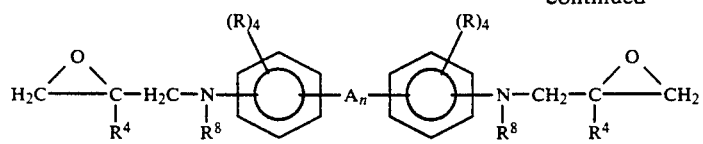

wherein R and n are as hereinbefore defined; each A is independently a direct single bond, a divalent hydrocarbyl group having from one to about 20, preferably from one to about 6, carbon atoms, —O—, —CO—, —SO—, —SO$_2$—, —S—, —S—S—, —CR$^7$=CR$^7$—, —C≡C—, —N=N—, —CR$^7$=N—, —N=CR$^7$—, —O—CO—, —CO—O—, —S—CO—, —CO—S—, —NR$^7$—CO—, —CO—NR$^7$—, —CR$^7$=N —N=CR$^7$—, —CO—CR$^7$=CR$^7$—. —CR$^7$=CR$^7$—CO—, —CO—O—N=CR$^7$—, —CR$^7$=N—O —OC—, —CO—O—N=CR$^7$—, —CO—NR$^7$—NR$^7$—OC—, —CR$^7$=CR$^7$—O—OC—, —CO—O—CR$^7$=CR$^7$—, —O —CO—CR$^7$=CR$^7$—, —CR$^7$=CR$^7$—CO—O—, —(CHR$^7$)$_{n'}$—O—CO—CR$^7$=CR$^7$—, —CR$^7$=CR$^7$—CO—O—(CHR$^7$)$_{n'}$—, —(CHR$^7$)$_{n'}$—CO—O—CR$^7$=CR$^7$, —CR$^7$=CR$^7$—O—CO—(CHR$^7$)$_{n'}$—, —CH$_2$—CH$_2$—CO—O—, —O—OC—CH$_2$—CH$_2$—, —C≡C—C≡C—, —CR$^7$=CR$^7$—CR$^7$=CR$^7$—, —CR$^7$=CR$^7$—C≡C, —C≡C—CR$^7$=CR$^7$—, —CR$^7$=CR$^7$—CH$_2$—O—OC—, —CO—O—CH$_2$—CR$^7$=CR$^7$—, —O—CO—C≡C—CO—O—, —O—CO—CR$^7$=CR$^7$—CO—O—, —O—CO—CH$_2$—CH$_2$—CO—O—, —S—CO—CR$^7$=CR$^7$—CO—S—, —CO—CH$_2$—NH—CO—, —CO—NH—CH$_2$—CO—, —NH—C(—CH$_3$)=CH—CO—, —CO—CH=C(—CH$_3$)—NH—, —CR$^7$=C(—Cl)—, —C(—Cl)=CR$^7$—, —CR$^7$C(—CN)—, —C(—CN)=CR$^7$—, —N=C(—CN)—, —C(—CN)=N—, —CR$^7$=C(—CN)—CO—O—, —O—CO—C(—CN)=CR$^7$—,

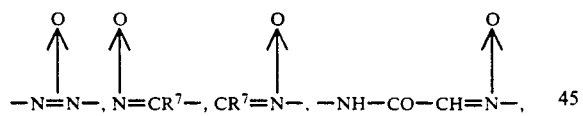

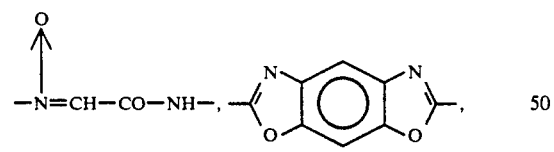

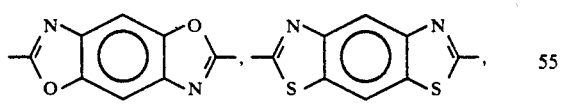

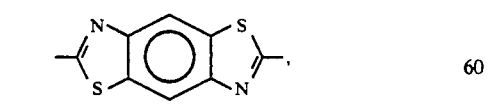

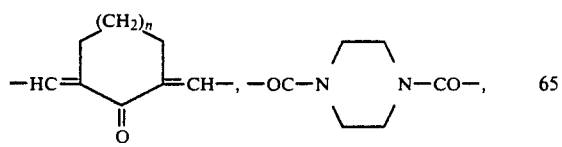

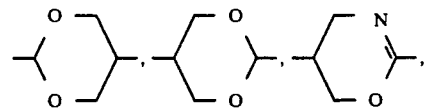

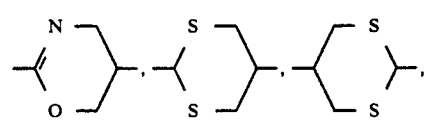

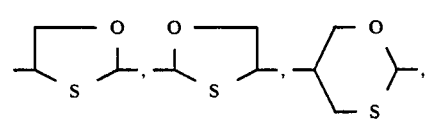

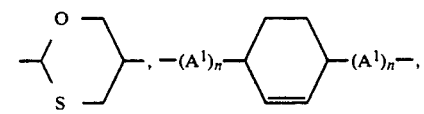

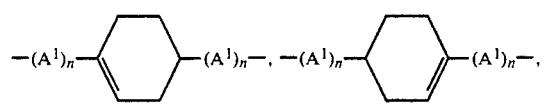

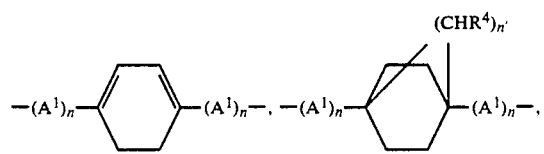

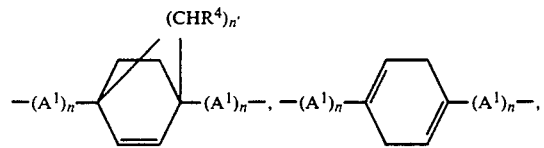

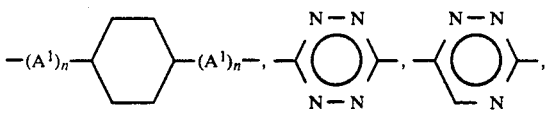

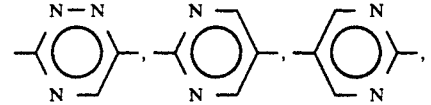

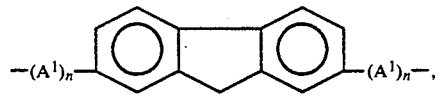

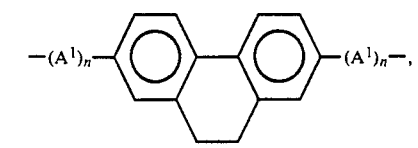

-continued

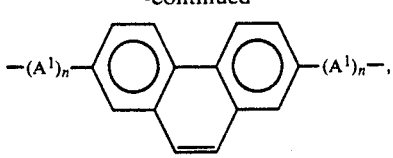

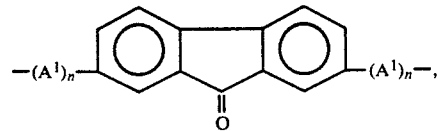

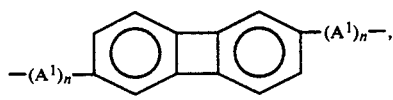

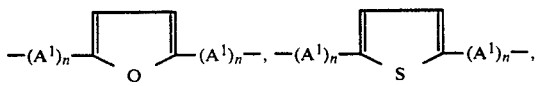

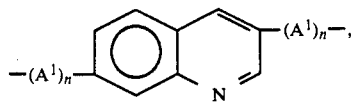

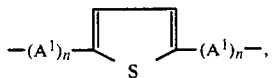

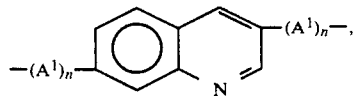

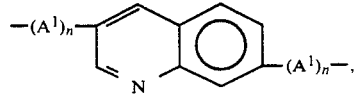

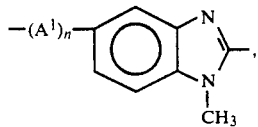

or

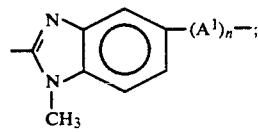

each A' is independently a divalent hydrocarbyl group having from one to about 10, preferably from 1 to about 6, more preferably from one to about 2, carbon atoms; A" is a divalent hydrocarbyl group having from one to about 6, preferably from one to about 4, more preferably from one to about 2, carbon atoms; each $A^1$ is independently a —CO—, —O—CO—, —CO—O—, —CO—S—, —S—CO—, —CO—$NR^7$— or —$NR^7$—CO—; each $R^4$ is independently hydrogen or a hydrocarbyl group having from one to about 3 carbon atoms; each $R^5$ is independently hydrogen, a hydrocarbyl group having from one to about 10, preferably from one to about 6, more preferably from one to about 3, carbon atoms or a halogen atom, preferably chlorine or bromine; each $R^6$ is independently hydrogen or a hydrocarbyl or halohydrocarbyl group having from one to about 6, preferably from 1 to about 4, more preferably from one to about 2 carbon atoms; Q is a direct bond, —$CH_2$—S—$CH_2$—, —$(CH_2)_{n''}$—, or

each $R^7$ is independently hydrogen or a hydrocarbyl group having from one to about 6, preferably from one to about 4, more preferably from one to about 2, carbon atoms, and is preferably hydrogen or a hydrocarbyl group containing one carbon atom; each $R^8$ is independently a hydrocarbyl group having from 1 to about 10, preferably from 1 to about 6, more preferably from 1 to about 2, carbon atoms or a

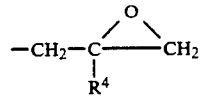

group; m has a value from about 0.001 to about 6, preferably from about 0.01 to about 3; m' has a value from one to about 10, preferably from one to about 4; n' has a value of one or two, n" has an average value of from about one to about 10; p has a value from zero to about 30, preferably from zero to about 5 and $p^1$ has a value of from one to about 30, preferably from one to about 3. The aromatic rings in Formulas III, IV, V, VI, VII, VIII, X and XI can also contain one or more heteroatoms selected from N, O, and S. The term "hydrocarbyl", when applied to the A" group of Formula VIII, can also include one or more heteroatoms selected from N, O, and S. Thus, A" may be, for example, the —CO— or —$CH_2$—O—$CH_2$— group.

Mesogenic epoxy resins include those represented by Formulas IV, VII, VIII and XI wherein each A is independently selected from the aforementioned listing, but with the proviso that A may not be a divalent hydrocarbyl group having from one to 20 carbon atoms, —O—, —CO—, —SO—, —$SO_2$—, —S—, —S—S— and with the proviso that at least 80 percent of the molecules are para substituted by the bridging groups (—A—) in Formulas IV, VII, XI and by the direct bond in Formula VIII, the substituent containing the glycidyl,

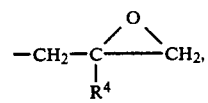

group(s), and the substituent containing the secondary hydroxyalkylidene, —$CH_2$—C(OH)($R^4$)—$CH_2$—, group(s) which are present when p or $p^1$ has a value greater than zero.

Representative epoxy resins include, for example, the diglycidyl ethers of: resorcinol, hydroquinone, 4,4'-isopropylidenediphenol (bisphenol A), 4,4'-dihydroxydiphenylmethane (bisphenol F), 4,4'-dihydroxybenzophenone, 3,3'5,5'-tetrabromo-4,4'-isopropylidenediphenol, 4,4'-thiodiphenol, 4,4'-sulfonyldiphenol, 4,4'-dihydroxydiphenyl oxide, 1,1-bis(4-hydroxyphenyl)-1-phenylethane, 3,3',5,5'-tetrachloro-4,4'-isopropylidenediphenol A, 3,3'-dimethoxy4,4'-isopropylidenediphenol, 4,4'-dihydroxy-alpha-methylstilbene, 4,4'-dihydroxybenzanilide, 4,4'-dihydroxyazoxybenzene, 4,4'-dihydroxybiphenyl, 4,4'-dihydroxydiphenylazomethine, 4,4'-dihydroxydiphenylacetylene, 4,4'-dihydroxystilbene, 4,4'-dihydroxy- alpha-cyanostilbene, 4,4'-dihydroxyazobenzene, 4,4'-dihydroxyazoxybenzene, 4,4'-dihydroxychalcone, 4-hydroxyphenyl-4-hydroxybenzoate; dipropylene glycol, poly(propylene glycol), thiodiglycol; the triglycidyl ether of tris(hydroxyphenyl)methane; the polyglycidyl ethers of a phenol or alkyl or halogen substituted phenol-aldehyde acid catalyzed condensation product (novolac resins); the tetraglycidyl amines of: 4,4'-diaminodiphenylmethane, 4,4'-diaminostilbene, N,N'-dimethyl-4,4'-diaminostilbene, 4,4'-diaminobenzanilide, 4,4'-diaminobiphenyl, 4,4'-diamino-alpha-methylstilbene; the polyglycidyl ether of the condensation product of: a dicyclopentadiene or an oligomer thereof and a phenol or alkyl or halogen substituted phenol; the advancement reaction products of the aforesaid di and polyglycidyl ethers with aromatic di and polyhydroxyl or carboxylic acid containing compounds including, for example, hydroquinone, resorcinol, catechol, 2,4-dimethylresorcinol, 4-chlororesorcinol, tetramethylhydroquinone, 4,4'-isopropylidenediphenol (bisphenol A), 4,4'dihydroxydiphenylmethane, 4,4'-thiodiphenol, 4,4'-sulfonyldiphenol, 2,2'-sulfonyldiphenol, 4,4'-dihydroxydiphenyl oxide, 4,4'-dihydroxybenzophenone, 1,1-bis(4-hydroxyphenyl)-1-phenylethane, 4,4'-bis(4(4-hydroxyphenoxy)-phenylsulfone)-diphenyl ether, 4,4'-dihydroxydiphenyl disulfide, 3,3',3,5'-tetrachloro-4,4'-isopropylidenediphenol, 3,3',3,5'-tetrabromo-4,4'-isopropylidenediphenol, 3,3'-dimethoxy-4,4'-isopropylidenediphenol, 4,4-dihydroxy-alpha-methylstilbene, 4,4'-dihydroxybenzanilide, bis(4-hydroxyphenyl)terephthalate, N,N'-bis(4-hydroxyphenyl)terephthalamide, bis(4'-hydroxybiphenyl)-terephthalate, 4,4'di-hydroxyphenylbenzoate, bis(4'-hydroxyphenyl)-1,4-benzenediimine; 1,1'-bis(4-hydroxyphenyl)cyclohexane, phloroglucinol, pyrogallol, 2,2',5,5'-tetrahydroxydiphenyl sulfone, tris(hydroxyphenyl)methane, dicyclopentadiene diphenol, tricyclopentadiene diphenol, terephthalic acid, isophthalic acid, 4,4'-benzanilidedicarboxylic acid, 4,4'-phenylbenzoatedicarboxylic acid, 4,4'-stilbenedicarboxylic acid, adipic acid; or any combination of the aforementioned epoxy resins and the like.

These epoxy resins can be prepared generally by reacting a di- or polyhydroxyl containing compound with an epihalohydrin in the presence of a suitable catalyst and in the presence or absence of a suitable solvent at a temperature suitably from about 0 deg. C. to about 100 deg. C., more suitably from about 20 deg. C. to about 80 deg. C., most suitably from about 20 deg. C. to about 65 deg. C.; at pressures suitably from about 30 mm Hg vacuum to about 100 psia., more suitably from about 30 Hg vacuum to about 50 psia., most suitably from about 60 mm Hg vacuum to about atmospheric pressure; for a time sufficient to complete the reaction, usually from about 0.5 to about 24, more usually from about 1 to about 12, most usually from about 1 to about 8 hours; and using from about 1.5:1 to 100:1, preferably from about 2:1 to about 50:1, most preferably from about 3:1 to about 20:1 moles of epihalohydrin per hydroxyl group. This initial reaction, unless the catalyst is an alkali metal or alkaline earth metal hydroxide employed in stoichiometric quantities, produces a halohydrin intermediate which is then reacted with a basic acting substance to convert the vicinal halohydrin groups to epoxide groups. The resultant product is a glycidyl ether compound.

Advancement reaction of di- and polyglycidyl ethers can be performed by the known methods which usually includes combining one or more suitable co ipounds having an average of more than one active hydrogen atom per molecule, including, for example, dihydroxy aromatic, dithiol or dicarboxylic acid compounds or compounds containing one primary amine or amide group or two secondary amine groups and the di- or polyglycidyl ethers in the presence or absence effect the advancement reaction. The epoxy resin and the compound having more than one active hydrogen atom per molecule are reacted in amounts which provide suitably from about 0.01:1 to about 0.95:1, more suitably from about 0.05:1 to about o.8:1, most suitably from about 0.10:1 to about 0.5:1 active hydrogen atoms per epoxy group. The advancement reaction can be conducted at atmospheric, superatmospheric or subatmospheric pressures at temperatures of from about 20 deg. C. to about 260 deg. C., more suitably from about 80 deg. C. to about 240 deg. C., most suitably from about 100 deg. C. to about 200 deg. C. The time required to complete the advancement reaction depends upon the temperature employed. Higher temperatures require shorter periods of time whereas lower temperatures require longer periods of time. Generally, times of from about 5 minutes to about 24 hours, more suitably from about 30 minutes to about 8 hours, most suitably from about 30 minutes to about 4 hours are employed. A catalyst, including, for example, phosphines, quaternary ammonium compounds, phosphonium compounds and tertiary amines, is frequently added to facilitate the advancement reaction and is usually employed in quantities of from about 0.01 to about 3, preferably from about 0.03 to about 1.5, most preferably from about 0.05 to about 1.5 percent by weight based upon the weight of the epoxy resin.

CURING AGENTS CURING CATALYSTS AND CURABLE BLENDS

The curable compositions of the present invention are prepared by mixing together one or more of the bis-(aminophenoxy)-alpha-substituted stilbene compositions with one or more epoxy resins and/or advanced epoxy resins, which all, none or a part of said epoxy resins and/or advanced epoxy resins may contain one or more mesogenic moities. The bis(aminophenoxy)-alpha-substituted stilbene compositions are employed in amounts which will effectively cure the mixture, with the understanding that the these amounts will depend upon the particular bis(aminophenoxy)-alpha-substituted stilbene and epoxy resin employed. Generally, suitable amounts are from about 0.80:1 to about 1.50:1, preferably from about 0.95:1 to about 1.05:1 equivalents of amine hydrogen in the bis(aminophenoxy)-alpha-substituted stilbene which is reactive with an epoxide group per equivalent of epoxide group in the epoxy resin at the conditions employed for curing.

The curing of the curable compositions of the present invention can be conducted at atmospheric, superatmospheric or subatmospheric pressures at temperatures of from about 0 deg. C. to about 300 deg. C., preferably from about 50 deg. C. to about 240 deg. C., more preferably from about 100 deg. C. to about 200 deg. C. The time required to complete curing depends upon the temperature employed. Higher temperatures require shorter periods of time whereas lower temperatures require longer periods of time. Generally, however, times of from about one minute to about 48 hours, preferably from about 15 minutes to about 8 hours, more preferably from about 30 minutes to about 3 hours are suitable.

It is also operable to partially cure (B-stage) the curable compositions of the present invention and then complete the curing at a later time. B-staging (partial cure) can be accomplished by heating at a temperature for a time such that only partial curing is produced. Usually, the cure temperatures are employed for B-staging;however for a shorter period of time. Generally, the extent of B-staging is monitored using analytical methods such as viscosity measurement, differential scanning calorimetry for residual cure energy or infrared spectrophotometric analysis for unreacted curable functional groups.

A preferred curable mixture of the present invention comprises a curing amount of one or more 4,4'-bis(4-aminophenoxy)-alpha-alkylstilbenes or N,N'-dialkyl-4,4'-bis(4-aminophenoxy)-alpha-alkylstilbenes with one or more epoxy resins containing one or more mesogenic moieties. An additional preferred curable mixture of the present invention comprises a curing amount of one or more 4,4'-bis(2-aminophenoxy)-alpha-alkylstilbenes or N,N'-dialkyl-4,4'-bis(2-aminophenoxy)-alpha-alkylstilbenes with one or more epoxy resins containing one or more mesogenic moieties. A likewise preferred curable mixture of the present invention comprises a curing amount of a combination of one or more 4,4'-bis(4-aminophenoxy)-alpha-alkylstilbenes or N,N'-dialkyl-4,4'-bis(4-aminophenoxy)-alpha-alkylstilbenes and one or more 4,4'-bis(2-aminophenoxy)-alpha-alkylstilbenes or N,N'-dialkyl-4,4'-bis(2-aminophenoxy)-alpha-alkylstilbenes with one or more epoxy resins containing one or more mesogenic moieties. Most preferred as the curable mixtures of the present invention are each of the aforementioned curable mixtures wherein said bis(aminophenoxy)-alpha-alkylstilbene and/or N,N'-dialkyl-bis(aminophenoxy)-alpha-alkylstilbene is the alpha-methylstilbene compound and the N,N'-dimethyl-alpha-methylstilbene compound, respectively, and the epoxy resin is the diglycidyl ether of 4,4'-dihydroxy-alpha-methylstilbene.

The curable mixtures of the present invention may also contain one or more of the known conventional curing agents and/or catalysts for curing epoxy resins, such as, for example, aliphatic, cycloaliphatic, polycycloaliphatic or aromatic primary monoamines; aliphatic, cycloaliphatic, polycycloaliphatic or aromatic primary and secondary polyamines; carboxylic acids and anhydrides thereof; aromatic hydroxyl containing compounds; imidazoles; guanidines; ureaaldehyde resins; melamine-aldehyde resins; alkoxylated urea-aldehyde resins; alkoxylated melamine-aldehyde resins; amidoamines; epoxy resin adducts all, none, or a part of which may contain one or more mesogenic moieties; combinations thereof and the like. Particularly suitable curing agents include, for example, methylenedianiline, 4,4'-diaminostilbene, 4,4'-diamino-alpha-methylstilbene, 4,4'-diaminobenzanilide, dicyandiamide, ethylene diamine, diethylenetriamine, triethylenetetramine, tetraethylenepentamine, urea-formaldehyde resins, melamine-formaldehyde resins, methylolated urea-formaldehyde resins, methylolated melamine-formaldehyde resins, phenol-formaldehyde novolac resins, cresol-formaldehyde novolac resins, sulfanilamide, diaminodiphenylsulfone, diethyltoluenediamine, t-butyltoluenediamine, bis-4-aminocyclohexylamine, isophoronediamine, diaminocyclohexane, hexamethylenediamine, piperazine, aminoethylpiperazine, 2,5-dimethyl-2,5-hexanediamine, 1,12-dodecanediamine, tris-3-aminopropylamine, combinations thereof and the like. If used a component of the curable mixtures of the present invention, from about 1 to about 99, preferably from about 1 to about 40, most preferably from about 1 to about 20 percent of the equivalents of amine hydrogen which are reactive with an epoxide group provided by the bis(aminophenoxy)-alpha-substituted stilbene are substituted using one or more of the aforesaid curing agents. This substitution is on an equivalent basis.

Particularly suitable curing catalysts include boron trifluoride, boron trifluoride etherate, aluminum chloride, ferric chloride, zinc chloride, silicon tetrachloride, stannic chloride, titanium tetrachloride, antimony trichloride, boron trifluoride monoethanolamine complex, boron trifluoride triethanolamine complex, boron trifluoride piperidine complex, pyridine-borane complex, diethanolamine borate, zinc fluoroborate, mixtures thereof and the like.

The curing catalysts are employed in amounts which will effectively cure the curable composition, however, these amounts will depend upon the particular bis(aminophenoxy)-alpha-substituted stilbene employed and the epoxy resin employed. Generally suitable amounts include, for example, 0.001 to about 2 percent by weight of the total epoxy resin used. It is frequently of benefit to employ one or more of the curing catalysts in the curing of the curable compositions of the present invention. This is generally done to accelerate or otherwise modify the curing behavior obtained when a curing catalyst is not used.

For the curable blends of one or more bis(aminophenoxy)-alpha-substituted stilbenes and one or more epoxy resins and/or advanced epoxy resins, when mesogenic moieties are present in one or more components of said blends other than the bis(aminophenoxy)-alpha-substituted stilbenes, it is frequently of value to B-stage the curable blend in order to chain extend the resin. This chain extension is required for some mesogen containing curable blends in order to achieve liquid crystal character. B-staging can also be employed to increase the temperature range at which a particular curable blend is liquid crystalline and to control the degree of crosslinking during the final curing stage.

ORIENTATION

For the curable blends of one or more bis(aminophenoxy)alpha-substituted stilbenes and one or more epoxy resins and/or advanced epoxy resins, when mesogenic moieties are present in one or more components of said blends, before and/or during processing and/or curing into a part, electric or magnetic fields, drawing and/or shear stresses can be applied for the purpose of orienting the liquid crystal moieties contained or developed therein which in effect improves the mechanical properties. As specific examples of these methods, Finkelmann, et al, Macromol. Chem., volume 180, pages 803-806 (March, 1979) induced orientation in thermotropic thermoplastic methacrylate copolymers containing mesogenic side chain groups decoupled from the main chain via flexible spacers in an electric field. Within the nematic liquid crystalline transition temperature range for one of the copolymers, homeotropic orientation was achieved with a half-time of approximately 10 seconds at 8 volts d.c. At higher voltages, turbulent flow disrupted the homeotropic orientation. A second copolymer within the nematic liquid crystalline transition temperature range gave reversible homeotropic orientation with an orientation time of less than 200 mseconds in a 50 Hz d.c. electric field. Threshold voltage was approximately 6 volts and the relaxation half-time was approximately 5 seconds. Thus, for the orientation of the curable blends of the present invention which contain or develop liquid crystal moieties, it is frequently of value to conduct simple preliminary experiments over the range of experimental conditions to be employed, including voltage to be applied and time to be used for application of the voltage to a given mesophase at a given temperature. In this manner, an indication of the critical electric field strength, orientation time and relaxation time for the mesophase to be oriented can be obtained and conditions not conducive to orientation, such as flow instability, can be avoided. Orientation of mesogenic side chain groups decoupled from the thermoplastic polymer main chain via flexible spacers in a magnetic field has been demonstrated by Roth and Kruecke, Macromol. Chem., volume 187, pages 2655–2662 (November, 1986). Within the broad temperature range of approximately −120 deg. C. to 200 deg. C., orientation of the polymers was observed (anisotropy in the motional processes as shown by change in line width of proton magnetic resonance signals as a function of temperature). In order to achieve macroscopic orientation in a magnetic field of about 2 T it was found that the choice of proper temperature is important such that the ordering effect of the magnetic field overcomes the disordering effect of thermal motion and that sufficient molecular mobility is present to allow for the ordering to occur. Furthermore, this proper temperature was found to vary as a function of the particular mesogen-containing polymer to be oriented. Thus, for the orientation of the curable blends of the present invention which contain or develop liquid crystal moieties, it is frequently of value to conduct simple preliminary experiments over the range of experimental conditions to be employed, including the magnetic field to be applied and time to be used for application of the magnetic field to a given mesophase at a given temperature. In this manner, an indication of the critical magnetic field strength, orientation time and relaxation time for the mesophase to be oriented can be obtained and conditions not conducive to orientation, such as improper temperature range, can be avoided. Magnetic field induced orientation of mesogenic main chain containing thermoplastic polymers has been demonstrated by Moore, et al, ACS Polymeric Materials Sciences and Engineering, volume 52, pages 84–86 (April-May, 1985). At the melt temperature for the liquid crystalline thermoplastic copolymer of p-hydroxybenzoic acid (80%) and polyethylene terephthalate (20%) the threshold for orientation was found to be approximately 0.4 T, with the degree of orientation (order parameter) depending on the strength of the magnetic field. Relaxation of the orientation once the polymer is removed from the magnetic field depends on the amount of time that the polymer spent in the magnetic field. Thus, for the liquid crystalline thermoplastic polymer maintained in a 6.3 T magnetic field, maximum relaxation time was approximately 15 minutes, while the liquid crystalline thermoplastic polymer maintained in a 2 T or less magnetic field exhibited a maximum relaxation time of less than one minute. An equation delineating the balance between the ordering effect of the magnetic field and the disordering effect of thermal motion is given for domains of radius a as follows:

$$X_a \cdot H_t^2 \cdot a^2 = kT/a$$

where $H_t$ is the threshold magnetic field and $X_a$ is the difference between the magnetic susceptibilities of the polymer when aligned parallel and perpendicular to the field. Magnetic and electric field orientation of low molecular weight mesogenic compounds is discussed by W. R. Krigbaum in *Polymer Liquid Crystals*, pages 275–309 (1982) published by Academic Press, Inc.

In addition to orientation by electric or magnetic fields, polymeric mesophases can be oriented by shear forces, for example, using shear rates as low as 0.1 sec$^{-1}$ to as high as 10,000 sec$^{-1}$, which are induced by drawing and/or flow through dies, orifices and mold gates. A general discussion for orientation of thermotropic liquid crystal polymers by this method is given by S. K. Garg and S. Kenig in *High Modulus Polymers*, pages 71–103 (1988) published by Marcel Dekker, Inc. and S. Keneg, Polymer Engineering and Science, volume 29, number 16, pages 1136–1141 (August, 1989). For the orientation by shear forces of the curable blends of the present invention which contain or develop liquid crystal moieties, it is frequently of value to conduct simple preliminary experiments over the range of experimental conditions to be employed, including total shear strain to be applied and time to be used for application of the shear force to a given mesophase at a given temperature. In this manner, an indication of the critical total shear strain, orientation time and relaxation time for the mesophase to be oriented can be obtained and conditions not conducive to orientation, such as tumbling of domain structure, can be avoided. For the mesomorphic systems based on the curable blends of one or more bis(aminophenoxy)-alpha-substituted stilbenes and one or more epoxy resins and/or advanced epoxy resins, this shear orientation can be produced by processing methods such as injection molding, extrusion, pultrusion, filament winding, filming and prepreging.

OTHER COMPONENTS

The curable blends of one or more bis(aminophenoxy)-alpha-substituted stilbenes and one or more epoxy resins and/or advanced epoxy resins, can be blended with other materials such as solvents or diluents, fillers, pigments, dyes, flow modifiers, thickeners, reinforcing agents, mold release agents, wetting agents, stabilizers, fire retardant agents, surfactants or any combination thereof and the like.

These additives are added in functionally equivalent amounts, e.g., the pigments and/or dyes are added in quantities which will provide the composition with the desired color; however, they are suitably employed in amounts of from about zero to about 20, more suitably from about 0.5 to about 5, most suitably from about 0.5 to about 3 percent by weight based upon the weight of the total blended compositions.

Solvents or diluents which can be employed herein include, for example, hydrocarbons, ketones, glycol ethers, aliphatic ethers, cyclic ethers, esters, amides, combinations thereof and the like. Particularly suitable solvents or diluents include, for example, toluene, xylene, methylethylketone, methylisobutylketone, diethylene glycol methyl ether, dipropylene glycol methyl ether, dimethylformamide, N-methylpyrrolidinone, tetrahydrofuran, dioxane, propylene glycol methyl ether or any combination thereof and the like.

The modifiers such as thickeners, flow modifiers and the like can be suitably employed in amounts of from zero to about 10, more suitably from about 0.5 to about 6, most suitably from about 0.5 to about 4 percent by weight based upon the weight of the total composition.

Reinforcing materials which can be employed herein include natural and synthetic fibers in the form of woven fabric, mats, monofilament, multifilament, unidirectional fibers, rovings, random fibers or filaments, inorganic fillers or whiskers, hollow spheres, and the like. Suitable reinforcing materials include glass, ceramics, nylon, rayon, cotton, aramid, graphite, polyalkylene terephthalates, polyethylene, polypropylene, polyesters or any combination thereof and the like.

Suitable fillers which can be employed herein include, for example, inorganic oxides, ceramic microspheres, plastic microspheres, glass microspheres, inorganic whiskers, calcium carbonate or any combination thereof and the like.

The fillers can be employed in amounts suitably from about zero to about 95, more suitably from about 10 to about 80, most suitably from about 40 to about 60 percent by weight based upon the weight of the total composition.

The curable blends of one or more bis(aminophenoxy)-alpha-substituted stilbenes and one or more epoxy resins and/or advanced epoxy resins of the present invention can be employed in coating, casting, encapsulation, electronic or structural laminate or composite, filament winding, molding, and the like applications.

The following examples are illustrative of the present invention, but are not to be construed as to limiting its scope in any manner.

EXAMPLE 1

A. Synthesis of 4,4'-Dihydroxy-alpha-methylstilbene

Phenol (1882 grams, 20.0 moles), chloroacetone (383.7 grams, 4.0 moles as chloroacetone) and methylene chloride (1.8 liters) are added to a 5 liter glass reactor equipped with a chilled water condenser, mechanical stirrer, nitrogen purge (one liter per minute), thermometer, dropping funnel and jacket for circulating coolant over the reactor exterior. Stirring commences concurrent with cooling of the reactant solution to $-10$ deg. C. The chloroacetone used is a commercial grade containing 96.5% chloroacetone, 2.85% 1,1-dichloroacetone, 0.60% mesityl oxide and 0.05% acetone. Concentrated sulfuric acid (392.3 grams, 4.0 moles) is added to the dropping funnel, then dropwise addition to the stirred reactant solution commences over a three hour period and so as to maintain the reaction temperature between $-10$ deg. C. and $-12$ deg. C. After 16 hours of post reaction at $-10$ deg. C. to $-12$ deg. C., the opaque, pale pink colored product is recovered and divided equally into three 2 liter glass speararory funnels. The contents of each separatory funnel are washed four times each with 500 milliliter portions of deionized water. The combined organic layers are recovered and divided equally into a pair of 4 liter glass beakers. The contents of each beaker is stirred, ethanol (400 milliliters) is added, deionized water (250 milliliters) is added and heating commences. Once a temperature of 70 deg. C. is achieved and substantially all of the methylene chloride solvent has boiled off, heating ceases and deionized water is added to each beaker in an amount sufficient to produce a total volume of 3.8 liters. Stirring is maintained for the next 6 hours during which time a crystalline slurry forms in each beaker. At this time, stirring is stopped and the crystalline slurry is chilled to 5 deg. C. and held therein for 14 hours. The crystalline product is recovered via filtration of the chilled crystalline slurry then added to a glass beaker and combined therein with deionized water (one liter). Stirring and heating commence until the stirred slurry reaches 100 deg. C. After 15 minutes at 100 deg. C., the stirred slurry is filtered through a fritted glass filter. The product recovered from the filter is dried in a vacuum oven at 80 deg. C. and one mm Hg to a constant weight of 549.7 grams of pale pink colored crystalline product. Proton magnetic resonance spectroscopy, Fourier transform infrared spectrophotometric analysis and high pressure liquid chromatography-mass spectrometry confirm the product structure.

B. Synthesis and Characterization of 4.4'-bis(4-Nitrophenoxy)-aloha-methylstilbene 4,4'-Dihydroxy-alpha-methylstilbene (11.3 grams, 0.10 equivalent) from B above, p-chloronitrobenzene (18.9 grams, 0.12 mole), $-325$ mesh anhydrous potassium carbonate (17.2 grams, 0.125 mole) and N,N-dimethylformamide (150 mililiters) are added to a reactor and stirred under a nitrogen atmosphere with heating to reflux (154 deg. C.). After 6 hours, at the reflux, high pressure liquid chromatographic analysis demonstrates that complete conversion of the 4,4'-dihydroxy-alpha-methylstilbene to a single major product has occurred. At this time, the reaction slurry is cooled to room temperature (24 deg. C.), filtered, then rotary evaporated to provide a solid product. The solid is slurried into a minimum of toluene, stirred, then filtered. The product recovered from the filter is dried in a vacuum oven at 80 deg. C. and one mm Hg to a constant weight of 14.0 grams of light yellow colored crystalline product. The melting point of the product measured in a glass capillary tube is 155 -157 deg. C. and has a turbid appearance. Continued heating to above 160 deg. C. provides a clear melt. Differential scanning calorimetry is completed using portions (9.0 and 9.1 milligrams) of the product and a heating rate of 10 deg. C. per minute under a stream of nitrogen flowing at 35 cubic centimeters per minute and a temperature from 30 deg. C. to 250 deg. C. A single sharp endotherm is obtained with a minimum at 161.9 deg. C. and an enthalpy of 77.2 joules per gram (average of two samples). Analysis of a portion of the product via microscopy under a crosspolarized light source is completed using a microscope equipped with a programmable hot stage using a heating rate of 10 deg. C. per minute and 70X magnification. The following results are obtained: at 30 deg. C., the product is a birefringent crystalline solid; at 152.5 deg. C. the first fluidity is observed; at 157.5 deg. C., the product appears as crystals dispersed in an isotropic fluid; isotropization is complete at 160 deg. C., with a trace amount of birefringence apparent in the fluid and a minor amount of birefringent specks also present therein. Upon cooling from 170 deg. C., crystallization occurs at 112.7 deg. C. Fourier transform infrared spectrophotometric analysis of a potassium bromide pellet of the product reveals the presence of the expected assymetric nitro group stretching at 1510 cm$^1$, the symmetric nitro group stretching at 1344 cm$^{-1}$, aromatic C—O vibration at 1244 cm$^{-1}$ and C—H out-of-plane deformation at 879 cm$^{-1}$ for the R$_2$C=CHR group.

C. Synthesis and Characterization of 4,4'-bis(4-Aminophenoxy)-aloha-methylstilbene 4,4'-bis(4-nitrophenoxy)-alpha-methylstilbene (11.7 grams, 0.05 nitro equivalent) from B above and ethyl acetate (200 milliliters) are added to a 400 milliliters heavy walled glass bottle and then sparged with nitrogen. After removal of the air by nitrogen sparging, Raney nickel catalyst (5.0 gram of a 50% wt. slurry in water at pH 10 washed once with deionized water) is added to the bottle which is then stoppered and multiply purged with hydrogen to replace the nitrogen atmosphere. The bottle is then placed on a shaking type agitator and pressurized to 50 psig with hydrogen. Shaking of the pressurized bottle at room temperature (24 deg. C.) commences until 28 minutes later, the hydrogen pressure reading indicates that 12.5 psig of hydrogen has been consumed. After an additional 7 minutes under hydrogen pressure, no further hydrogen uptake occurs and the reaction slurry is recovered and filtered to remove the Raney nickel, then rotary evaporated to provide a solid product (9.5 grams). The softening point of a portion of the product measured in a glass capillary tube is 135 deg. C. with melting observed at 148-150 deg. C. Differential scanning calorimetry is completed using portions (9.8 and 9.5 milligrams) of the product and a heating rate of 10 deg. C. per minute under a stream of nitrogen flowing at 35 cubic centimeters per minute and a temperature range from 30-250 deg. C. A pair of endotherms are obtained with minima at 138.9 deg. C. and 159.9 deg. C. and enthalpies of 15.9 joules per gram and 86.3 joules per gram, respectively (average of two samples). Analysis of a portion of the product via microscopy under a crosspolarized light source is completed using a microscope equipped with a programmable hot stage using a heating rate of 10 deg. C. per minute and 70X magnification. The following results are obtained: at 30 deg. C., the product is a birefringent crystalline solid; at 139 deg. C., softening is observed; at 152 deg. C., the first fluidity is observed; between 152-157 deg. C., the product appears as crystals dispersed in an isotropic fluid; isotropization is complete at 157 deg. C., with a minor amount of birefringent specks present in the fluid. Upon cooling from 165 deg. C., crystallization occurs at 87 deg. C. Fourier transform infrared spectrophotometric analysis of a potassium bromide pellet of the product reveals the presence of the expected primary amine group N—H stretching at 3396, 3336 and 3216 (shoulder) cm$^{-1}$ concurrent with the complete disappearance of the assymetric and symmetric nitro group stretching, C—H stretching absorbance of the aromatic rings and =C—H at 3044 cm$^{-1}$, NH$_2$ deformation at 1629 cm$^{-1}$, absorbance in the C=C stretching region at 1603 cm$^{-1}$, aromatic ring stretching absorbance at 1503 cm$^{-1}$, aromatic C—O vibration at 1238 cm$^{-1}$, (shoulder at 1278 cm$^{-1}$ due to aromatic C—N stretch vibration), C—H out-of-plane deformation at 879 cm$^{-1}$ for the R$_2$C=CHR group and out-of-plane C—H bending vibration at 826 (846 shoulder) cm$^{-1}$ indicative of paradisubstitution. Decoupled C$^{13}$ nuclear magnetic resonance spectroscopic analysis reveals a complete lack of peaks in the chemical shift range of 0 to 115 ppm (versus tetramethylsilane), except a single peak at 17.1 ppm due to the alpha —CH$_3$ on the stilbene linkage, thus demonstrating the integrity of the stilbenic unsaturation. Titration of a portion of the product provides a 99.35 —NH equivalent weight versus a theoretical 102.12 equivalent weight.

EXAMPLE 2

A. Synthesis of 4,4'-Diglycidyloxy-alpha-methylstilbene 4,4'-Dihydroxy-alpha-methylstilbene (452.5 grams, 4.0 hydroxyl equivalents) prepared using the method of Example 1-A, epichlorohydrin (1850.6 grams, 20.0 moles), deionized water (160.9 grams, 8.0 percent by weight of the epichlorohydrin used) and isopropanol (996.5 grams, 35 percent by weight of the epichlorohydrin used) are added to a reactor and heated to 50 deg. C. with stirring under a nitrogen atmosphere. Once the 50 deg. C. temperature is achieved, sodium hydroxide (144.0 grams, 3.60 moles) dissolved in deionized water (576.0 grams) is added dropwise to the reactor over a 45 minute period and so as to induce an exothermic increase in temperature to 63 deg. C., with subsequent maintenance of the temperature at 55 deg. C. Ten minutes after completion of the aqueous sodium hydroxide addition, the stirring is stopped and the aqueous layer which separates from the reaction mixture is pipetted off and discarded. Stirring is resumed and after a total of 20 minutes following the completion of the initial aqueous sodium hydroxide addition, a second solution of aqueous sodium hydroxide (64.0 grams, 1.60 mole) dissolved in deionized water (256.0 grams) is added to the reactor over a 20 minute period with maintenance of the 53 deg. C. reaction temperature. Fifteen minutes after completion of the aqueous sodium hydroxide, the recovered reaction mixture is added to a pair of 2 liter separatory funnels and each portion washed with warm (60-70 deg. C.) deionized water (375 milliliters). The separated organic layers are washed a second and third time (375 milliliters of warm deionized water is used for each washing), recovered and then rotary evaporated under vacuum using final conditions of 150 deg. C. and one mm Hg for 2 hours. After removal from the rotary evaporator, the molten epoxy resin is vacuum filtered through a heated (175 deg. C.) medium fritted glass funnel, then poured into an aluminum foil tray to solidify. The 4,4'-diglycidyloxy-alpha-methylstilbene is recovered (648.1 grams) as a crystalline white solid. Titration of portions of the diglycidyl ether product reveals an epoxide equivalent weight (EEW) of 178.56. Analysis of a portion of the diglycidyl ether product via microscopy under crosspolarized light is completed at 70X magnification using a microscope equipped with a programmable hot stage using a heating rate of 10 deg. C. per minute and a range of 30 to 150 deg. C., immediately followed by cooling. Isotropization is observed at 128-129 deg. C., liquid crystallinity occurs at 95 deg. C. and crystallization occurs at 66 deg. C. The diglycidyl ether gives monotropic liquid crystallinity with a nematic liquid crystalline texture.

B. Preparation and Copolymerization of a Curable Blend of 4,4'-bis(4-Aminophenoxy)-alpha-methylstilbene and 4,4'-Diglycidyloxy-alpha-methylstilbene A portion (0.1211 gram, 0.001219 —NH equivalents) of 4,4'bis(4-aminophenoxy)-alpha-methylstilbene from Example 1-C and a portion (0.2177 gram, 0.001219 epoxide equivalents) of 4,4'-diglycidyloxy-alpha-methylstilbene from A above are dissolved in methylene chloride (3 milliliters). The solution is devolatilized under a nitrogen sparge, then dried in a vacuum oven at 25 deg. C. and one mm Hg to a constant weight. Differential scanning calorimetry is completed using portions (11.9 and 10.4 milligrams) of the blend and a heating rate of 10 deg. C. per minute under a stream of nitrogen flowing at 35 cubic centimeters per minute and a temperature range from 30 to 250 deg. C. An endotherm is obtained with a minimum at 108.4 deg. C. and an enthalpy of 79.2 joules per gram. An exotherm is obtained with a maximum at 176.3 deg. C. and an enthalpy of 307.7 joules per gram (average of two samples). A second heating is completed using the aforementioned conditions with no residual cure energy and no glass transition temperature observed. Analysis of the pale yellow colored, transparent cured product recovered from the differential scanning calorimetry analysis via microscopy under crosspolarized light is completed and reveals the presence of a nematic liquid crystalline texture. Analysis of a portion of the curable blend via microscopy under crosspolarized light is completed using a microscope equipped with a programmable hot stage using a following results are obtained: at 30 deg. C., the blend is a birefringent crystalline solid; at 89 deg. C., softening is first observed; at 98 deg. C., fluidity is first observed; at 102 deg. C., the blend is an isotropic fluid containing birefringent crystals; at 122 deg. C., isotropization is complete; at 155 deg. C., the fluid becomes highly viscous; at 159 deg. C., numerous birefringent specks form; at 172 deg. C., thermosetting occurs with retention of the birefringent specks. A second portion of the blend is analyzed using the aforementioned conditions with heating to 165 deg. C. and is found to be highly birefringent and stir opalescent when removed from the hot stage at this temperature and allowed to cool. A third portion of the blend between a glass slide and coverslip is placed on the stage which is preheated to 165 deg. C. After 40 seconds a viscous isotropic fluid forms. The sample is removed from the heated stage at this time and sheared between the coverslip and slide while cooling, resulting in opalescence. Once cooled to room temperature (24 deg. C), the solid is observed by microscopy under crosspolarized light and found to possess a mixture of textures, including smectic liquid crystalline texture.

EXAMPLE 3

Preparation of a Casting from a Curable Blend of 4.4'-bis(4-Aminophenoxy)-aloha-methylstilbene and 4.4 -Diglycidyloxy-aloha-methylstilbene A portion (3.97 grams, 0.0399 -NH equivalents) of 4,4'bis(4-aminophenoxy)-alpha-methylstilbene from Example 1-C and a portion (7.13 grams, 0.0399 epoxide equivalents) of 4,4'-diglycidyloxy-alpha-methylstilbene from Example 2-A are dissolved in methylene chloride (30 milliliters). The solution is devolatilized under a nitrogen sparge, then dried in a vacuum oven at 25 deg. C. and one mm Hg to a constant weight. A portion (0.85 gram) of the curable blend is placed in an aluminum dish then put into an oven preheated to 140 deg. C. After one minute, a partial melt is achieved and is stirred. After a total of 2 minutes, a translucent viscous liquid is obtained. After a total of 5 minutes, the viscous translucent liquid resin is transferred to an oven preheated to 120 deg. C. After a total of 11 minutes, the resin gels to an opaque solid. After a total of 3 hours at 120 deg. C., the temperature in the oven is increased by 20 deg. C. every hour. After 180 deg. C. is achieved, the temperature in the oven is increased to 200 deg. C. and maintained therein for the next four hours. After cooling the oven, the recovered casting is opaque. Microscopy under crosspolarized light reveals the presence of birefringent domains and liquid crystal textures. Differential scanning calorimetry is completed using portions (60 and 60 milligrams) of the cured casting and a heating rate of 10 deg. C. per minute under a stream of nitrogen flowing at 35 cubic centimeters per minute and a temperature range from 30 to 300 deg. C. No glass transition temperature or any other events are observed (average of two samples).

EXAMPLE 4

Preparation of An Injection Molded Casting from a Curable Blend of 4,4'-bis(4-Aminopheoxy)-alpha-methylstilbene and 4,4'-Diglycidyloxy-alpha-methylstilbene A portion (6.5 grams) of the curable blend from Example 3 is placed into the reservoir of an injection molder preheated to 145 deg. C. Periodic stirring commences and after a total of 4 minutes in the reservoir, a translucent melt is obtained. After an additional minute of heating in the reservoir, the resin is injected through a 0.020 inch by 0.375 inch (0.5 by 9.5 mm) rectangular flow gate into a mold preheated to 80 deg. C. and having the following dimensions: 3.0 inches by 0.5 inch by 0.125 inch (76.2 by 12.7 by 3.125 mm). At the time of injection molding, a sample of the resin is removed from the reservoir and cooled to room temperature (23 deg. C.). A portion of this sample removed before cooling is placed on a stage preheated to 145 deg. C. and examined by microscopy under crosspolarized light at 70X magnification. This microscopic examination reveals the presence of a dispersed birefringent phase and phase segregated regions which have liquid crystal textures. After 15 seconds at 145 deg. C., cooling at a rate of 10 deg. C. per minute commences. At 132 deg. C., an increase in the birefringent phase is observed. At 130 deg. C., the resin is opaque and barely mobile. At this time, shearing of the resin by moving the glass coverslip over the slide produces birefringent striations in the direction that the shear is applied. Portions (21.4 and 12.7 milligrams) of the sample removed from the reservoir at the time of injection molding are analyzed by differential scanning calorimetry using a heating rate of 10 deg. C. per minute under a stream of nitrogen flowing at 35 cubic centimeters per minute and a temperature range from 30 to 300 deg. C. An exotherm is obtained with a maximum at 139.9 deg. C. and an enthalpy of 168.4 joules per gram. The mold is removed from the injection molder immediately after completion of the resin injection then placed in an oven preheated to 80 deg. C. After a total of 3 hours at 80 deg. C., the temperature in the oven is increased by 20 deg. C. every hour. After 160 deg. C. is achieved, the temperature in the oven is increased to 180 deg. C. and maintained therein for the next 4 hours. After cooling the oven, the recovered casting is opaque and contains birefringent domains when viewed by microscopy under crosspolarized light at 70X magnification. Differential scanning calorimetry is completed using portions (60 and 60 milligrams) of the cured casting and a heating rate of 10 deg. C. per minute under a stream of nitrogen flowing at 35 cubic centimeters per minute and a temperature range from 30 to 300 deg. C. No glass transition temperature or any other events are observed (average of two samples).

EXAMPLE 5

Preparation of a Casting from a Curable Blend of 4,4'-bis(4-Aminopheoxy)-alpha-methylstilbene and Diglycidyl Ether of Bisphenol A A portion (2.382 grams. 0.0233 -NH equivalents) of 4.4'-bis(4-aminopheoxy)-alpha-methylstilbene (102.1 —NH equivalent weight) prepared using the method of Example 1-C and a portion (4.046 grams, 0.0233 epoxide equivalents) of diglycidyl ether of bisphenol A (173.39 epoxide equivalent weight) are mixed in an aluminum pan to a homogeneous paste. Analysis of a portion of the blend via microscopy under a crosspolarized light source is completed using a microscope equipped with a programmable hot stage using a heating rate of 10 deg. C. per minute an 70X magnification. The following results are obtained: at 30 deg. C., the product is a slurry of birefringent crystalline diamine dispersed in the epoxy resin, at 97 deg. C., the diamine crystals are beginning to dissolve; at 112 deg. C., in excess of 95% of the diamine crystals are dissolved with mixing; at 117–124 deg. C., all remaining diamine crystals have dissolved. Once 130 deg. C. is reached, cooling at a rate of 10 deg. C. per minute commences until 45 deg. C. is reached. At this time, a dispersed birefringent phase is observed in the translucent viscous resin. Portions (15.9 and 23.3 milligrams) of the curable blend are analyzed by differential scanning calorimetry using a heating rate of 10 deg. C. per minute under a stream of nitrogen flowing at 35 cubic centimeters per minute and a temperature range from 30 to 300 deg. C. An exotherm is obtained with a maximum at 179.1 deg. C. and an enthalpy of 311.9 joules per gram (average of two samples). The remaining curable blend is placed in an aluminum dish then put into an oven preheated to 145 deg. C. After a total of 4 minutes, a translucent viscous liquid is obtained and the temperature in the oven is reduced to 120 deg. C. After fours at 120 deg. C., the temperature in the oven is increased by 20 deg. C. every hour. After 180 deg. C. is achieved, the temperature in the oven is increased to 200 deg. C. and maintained therein for the next 4 hours. After cooling the oven, the recovered casting is translucent and slightly hazy. Microscopy under crosspolarized light reveals the presence of birefringent liquid crystal textures. Differential scanning calorimetry is completed using portions (40 and 40 milligrams) of the cured casting and a heating rate of 10 deg. C. per minute under a stream of nitrogen flowing at 35 cubic centimeters per minute and a temperature range from 3o to 300 deg. C. A glass transition temperature of 179.4 deg. C. is detected (average of two samples).

EXAMPLE 6

Dynamic Mechanical Analysis Of an Injection Molded Casting from a Curable Blend of 4,4'-bis(4-Aminophenoxy)-alpha-methylstilbene and 4,4'-Diglycidyloxy-alpha-methylstilbene A portion (31.33 by 3.84 by 3.09 mm) of the injection molded casting from Example 4 is subjected to dynamic mechanical analysis in the resonant mode using standard methods (ASTM D 4065-82). A 5 deg. C. per minute rate of heatup is employed with a temperature range of 30 to 250 deg. C. Storage modulus (E') values thus determined are as follows for selected temperatures. The maximum temperature observed for the tan delta transition is 168.6 deg. C.

| Temperature (deg. C.) | Storage Modulus (GPa) |
| --- | --- |
| 35 | 2.814 |
| 93 | 1.744 |
| 121 | 1.388 |
| 149 | 0.9658 |
| 177 | 0.4611 |
| 204 | 0.3016 |
| 232 | 0.2498 |

EXAMPLE 7

A. Synthesis of 4,4'-bis(2-Nitrophenoxy)-alpha-methylstilbene 4,4'-Dihydroxy-alpha-methylstilbene (22.6 grams, 0.20 hydroxyl equivalent) from Example 1-B, o-chloronitrobenzene (39.4 grams, 0.25 mole), −325 mesh anhydrous potassium carbonate (34.5 grams, 0.25 mole) and N,N-dimethylformamide (200 mililiters) are added to a reactor and stirred under a nitrogen atmosphere with heating to 130 deg. C. After 9 hours at the 130 deg. C. temperature, high pressure liquid chromatographic analysis demonstrates that complete conversion of the 4,4'-dihydroxy-alpha-methylstilbene to a single major product has occurred. At this time, the reaction slurry is cooled to room temperature (24 deg. C.), filtered, then rotary evaporated to a constant weight of 53.6 grams of reddish brown colored liquid product.

B. Synthesis and Characterization of 4,4'-bis(2-Aminophenoxy)-alpha-methylstilbene 4,4'-bis(2-Nitrophenoxy)-alpha-methylstilbene (48.6 grams. 0.2075 nitro equivalent) from B above and ethyl acetate (500 milliliters) are added to a one liter stainless steel pressure bottle and then sparged with nitrogen. After removal of the air by nitrogen sparging, Raney nickel catalyst (10.0 gram of a 50% wt. slurry in water at pH 10 washed twice with with 25 milliliter portions of deionized water then twice with 25 milliliter portions of isopropanol) is added to the bottle which is then stoppered and multiply purged with hydrogen to replace the nitrogen atmosphere. The bottle is then placed on a shaking type agitator and presurrized to 50 psig with hydrogen. Shaking of the pressurized bottle at room temperature (24 deg. C.) commences until 106 minutes later, the hydrogen pressure reading indicates that 44 psig of hydrogen has been consumed. After an additional 15 minutes under hydrogen pressure, no further hydrogen uptake occurs and the reaction slurry is recovered and filtered to remove the Raney nickel, then rotary evaporated to provide a total volume of 100 milliliters. n-Hexane (100 milliliters) is added to the concentrated solution followed by cooling in an ice bath. The solid precipitate is recovered by filtration then washed with a minimum of a 1:1 volume mixture of ethyl acetate:n-hexane. The product recovered from the filter is dried in a vacuum oven at 80 deg. C. and one mm Hg to a constant weight of 28.7 grams of light amber colored product. The melting point of a portion of the product measured in a glass capillary tube is observed at 104–106 deg. C. Differential scanning calorimetry is completed using portions (9.5 and 8.1 milligrams) of the product and a heating rate of 10 deg. C. per minute under a stream of nitrogen flowing at 35 cubic centimeters per minute and a temperature range from 30–160 deg. C. An endotherm is obtained with a minimum at 109.7 deg. C. and an enthalpy of 74.0 joules per gram (average of two samples). Analysis of a portion of the product via microscopy under a crosspolarized light source is completed using a microscope equipped with a programmable hot stage using a heating rate of 10 deg. C. per minute and 70X magnification. The following results are obtained: at 30 deg. C., the product is a birefringent crystalline solid; at 99 deg. C., softening is observed; at 100 deg. C., the product appears as crystals dispersed in an isotropic fluid; isotropization is complete at 107.4 deg. C. Upon cooling from 110 deg. C., initial crystallization is observed at 61 deg. C. Fourier transform infrared spectrophotometric analysis of a neat film of the product on a potassium chloride plate reveals the presence of the expected primary amine group N—H stretching at 3469, 3376 and 3210 cm$^{-1}$ concurrent with the complete disappearance of the assymetric and symmetric nitro group stretching, C—H stretching absorbance of the aromatic rings and =C—H at 3037 (3044 shoulder) cm$^{-1}$, NH$_2$ deformation at 1616 cm$^{-1}$, absorbance in the C=C stretching region at 1603 cm$^{-1}$, aromatic ring stretching absorbance at 1503 cm$^{-1}$, aromatic C—O vibration at 1224 cm$^{-1}$, (shoulder at 1271 cm$^{-1}$ due to aromatic C—N stretch vibration), C—H out-of-plane deformation at 879 cm$^{-1}$ for the R$_2$C=CHR group, out-of-plane C—H bending vibration at 832 (846 slight shoulder) cm$^{-1}$ indicative of para-disubstitution and out-of-plane C—H bending vibration at 746 cm$^{-1}$ indicative of ortho-disubstitution. Decoupled C$^{13}$ nuclear magnetic resonance spectroscopic analysis reveals a complete lack of peaks in the chemical shift range of 0 to 115 ppm (versus tetramethylsilane), except a single peak at 17.5 ppm due to the alpha —CH$_3$ on the stilbene linkage, thus demonstrating the integrity of the stilbenic unsaturation. Proton magnetic resonance spectroscopic analysis (250 MHz) reveals a singlet at 2.25 ppm for the —CH$_3$, a broad singlet at 3.80 ppm and a multiplet between 6.7–7.47 ppm for the aromatic ring hydrogens and the stilbenic =C—H. Titration of a portion of the product provides a 103.357 —NH equivalent weight versus a theoretical 102.12 equivalent weight.

In a repeat of the aforementioned synthesis, 4,4′-bis(2-aminophenoxy)-alpha-methylstilbene (53.6 grams) is hydrogenated, the reaction slurry is recovered and filtered to remove the Raney nickel, then rotary evaporated at 120 deg. C. and one mm Hg until residual o-chloroaniline is removed. The light amber colored product thus recovered (40.4 grams) solidifies on standing. Titration of a portion of the product provides a 103.189 —NH equivalent weight versus a theoretical 102.12 equivalent weight.

EXAMPLE 8

Preparation and Copolymerization of a Curable Blend of 4,4′-bis(2-Aminophenoxy)-alpha-methylstilbene and 4.4′-Diglycidyloxy-alpha-methylstilbene A portion (6.17 grams, 0.0598 —NH equivalents) of 4,4′bis(2-aminophenoxy)-alpha-methylstilbene from Example 7-B and a portion (10.68 grams, 0.0598 epoxide equivalents) of 4,4′-diglycidyloxy-alpha-methylstilbene from Example 2-A are dissolved in methylene chloride (30 milliliters). The solution is devolatilized under a nitrogen sparge, then dried in a vacuum oven at 25 deg. C. and one mm Hg to a constant weight. Differential scanning calorimetry is completed using portions (12.9 and 19.5 milligrams) of the blend and a heating rate of 10 deg. C. per minute under a stream of nitrogen flowing at 35 cubic centimeters per minute and a temperature range from 30 to 300 deg. C. An endotherm is obtained with a minimum at 117.4 deg. C. and an enthalpy of 27.3 joules per gram. An exotherm is obtained with a maximum at 207.6 deg. C. and an enthalpy of 237.6 joules per gram (average of two samples). A second heating is completed using the aforementioned conditions with a glass transition temperature of 146.5 deg. C. and no residual cure energy observed Analysis of the translucent cured product recovered from the differential scanning calorimetry analysis via microscopy under crosspolarized light is completed using a microscope equipped with a programmable hot stage using a heating rate of 10 deg. C. per minute and 70X magnification. A high level of birefringence is observed. Analysis of a portion of the curable blend via microscopy under crosspolarized light is completed using a microscope equipped with a programmable hot stage using a heating rate of 10 deg. C. per minute and 70X magnification. The following results are obtained: at 30 deg. C., the blend is a birefringent crystalline solid; at 70 deg. C., partial melting is observed with dispersed crystals present; at 109 deg. C., partial clearing of the crystals is observed; at 124 deg. C., isotropization is complete. Heating is continued to 130 deg. C. and after 32 minutes thermosetting occurs to a non-birefringent transparent solid which exhibits birefringence when scratched with a steel needle. A second portion of the blend between a glass slide and coverslip is placed on the stage which is preheated to 130 deg. C. After 45 seconds an isotropic fluid forms and cooling at 10 deg. C. per minute commences, with the following results: at 82 deg. C., a minor amount of birefringent domains are observed; at 71 deg. C., a minor amount of liquid crystal texture is observed; at 60 deg. C., the resin is translucent; at 45 deg. C. the translucent resin is barely mobile. At this time, the sample is removed from the heated stage at this time and sheared between the coverslip and slide while cooling, resulting in no change in the morphology. Once cooled to room temperature (24 deg. C.), the tacky semi-solid is observed by microscopy under crosspolarized light and found be non-birefringent except for dispersed crystals present.

EXAMPLE 9

Preparation of a Casting form a Curable Blend of 4,4′-bis(2-Aminophenoxy)-alpha-methylstilbene and 4,4′-Diglycidyloxy-alpha-methylstilbene A portion (3.51 grams) of the curable blend of 4,4′-bis(4-aminophenoxy)-alpha-methylstilbene and 4,4′-diglycidyloxy-alpha-methylstilbene from Example 8 is placed in an aluminum dish then put into an oven preheated to 130 deg. C. After two minutes, a partial melt is achieved and is stirred. After a total of 10 minutes, a translucent viscous liquid is obtained. After a total of 15 minutes, the translucent viscous liquid is sampled for differential scanning calorimetry and microscopy. Once cooled to room temperature (24 deg. C.), microscopy under crosspolarized light reveals the presence of small birefringent domains and liquid crystal textures. Differential scanning calorimetry is completed using portions (22.3 and 20.2 milligrams) of the sample and a heating rate of 10 deg. C. per minute under a stream of nitrogen flowing at 35 cubic centimeters per minute and a temperature range from 30 to 300 deg. C. An endotherm is obtained with a maximum at 201.1 deg. C. and an enthalpy of 206.4 joules per gram (average of two samples). A second heating is completed using the aforementioned conditions with a glass transition temperature of 150.9 deg. C. and no residual cure energy observed. After 35 minutes, the resin is near the gel point such that fibers can be drawn therefrom with a cold spatula. Once cooled to room temperature (24 deg. C.), microscopy under crosspolarized light reveals a high level of birefringence in the fibers. A sample of the resin taken at this time and cooled to room temperature (24 deg. C.) is translucent and somewhat cloudy in appearance. Microscopy under crosspolarized light reveals the presence of dispersed birefringent domains and liquid crystal textures. A second portion of the sample of the resin taken at this time is placed between a glass slide and coverslip then placed on the stage of a microscope which has been preheated to 130 deg. C. Cooling at 10 deg. C. per minute commences until 80 deg. C. is reached, then the sample is removed from the heated stage and sheared between the coverslip and slide. The gelatinous semi-solid resin exhibits a high level of birefringence as a result of the shearing. Upon cooling to room temperature (24 deg. C.), the resin is a translucent solid which retains the high level of birefringence. After 45 minutes, the resin is a rubbery gel with a translucent, cloudy appearance. After a total of 3 hours at the 130 deg. C. temperature, the temperature is increased 20 deg. C. every hour until 200 deg. C. is achieved. The 200 deg. C. temperature is held for 4 hours after which time, the oven is allowed to gradually cool to room temperature (24 deg. C.) and the casting recovered and examined by microscopy under crosspolarized light A high level of birefringence is observed with a minor amount of a dispersed second phase. Differential scanning calorimetry is completed using portions (60.0 and 60.0 milligrams) of the casting and a heating rate of 10 deg. C. per minute under a stream of nitrogen flowing at 35 cubic centimeters per minute and a temperature range from 30 to 300 deg. C. A glass transition temperature of 159.3 deg. C. and no residual cure energy are observed (average of two samples).

EXAMPLE 10

Preparation of an Injection Molded Casting from a Curable Blend of 4,4'-bi(2-Aminophenoxy)-alpha-methylstilbene and 4,4'-Diglycidyloxy-alpha-methylstilbene A portion (7.07 grams) of the curable blend from Example 8 is placed into an oven preheated to 13D deg. C. and stirred periodically. After 12 minutes in :h° oven. meltinq has occurred and at this time, the resin is poured into the reservoir of an injection molder preheated to 130 deg. C. After a total of 7 minutes in the reservoir, fibers can be drawn from the molten resin with a cold spatula. After an additional four minutes of heating in the reservoir, heating of the reservoir ceases. After an additional minute, when the reservoir is at 128 deg. C. and the resin is near its gel point, the resin is injected through a 0.020 inch by 0.375 inch (0.5 by 9.5 mm) rectangular flow gate into a mold preheated to 80 deg. C. and having the following dimensions: 3.0 inches by 0.5 inch by 0.125 inch (76.2 by 12.7 by 3.125 mm). At the time of injection molding, a sample of the resin is removed from the reservoir and cooled to room temperature (24 deg. C.). A portion of this sample removed before cooling is placed on a stage preheated to 130 deg. C. and examined by microscopy under crosspolarized light at 70X magnification. This microscopic examination reveals the resin to be a viscous translucent non-birefringent liquid. After 15 seconds at 130 deg. C., cooling at a rate of 10 deg. C. per minute commences. At 100 deg. C., a low level of birefringence is observed. At this time, shearing of the resin by moving the glass coverslip over the slide produces no change in the morphology of the gelatinous mobile resin. At 80 deg. C., shear is again applied and produces a high level of birefringence in the barely mobile resin. This same morphology is maintained upon cooling to room temperature (24 deg. C.). Portions (14.6 and 21.3 milligrams) of the sample removed from the reservoir at the time of injection molding are analyzed by differential scanning calorimetry using a heating rate of 10 deg. C. per minute under a stream of nitrogen flowing at 35 cubic centimeters per minute and a temperature range from 30 to 300 deg. C. An exotherm is obtained with a maximum at 200.7 deg. C. and an enthalpy of 143.1 joules per gram (average of two samples). The mold is removed from the injection molder two hours after completion of the resin injection then placed in an oven preheated to 110 deg. C. After one hour at 110 deg. C., the temperature in the oven is increased by 10 deg. C. every hour. After 140 deg. C. is achieved, the temperature in the oven is increased by 20 deg. C. every hour. After 200 deg. C. is achieved, the temperature in the oven is maintained therein for the next 2 hours. After cooling the oven, the recovered casting is translucent and possesses a high level of birefringence when viewed by microscopy under crosspolarized light at 70X magnification. The flashing around the edges of the casting exhibits a flow oriented striated birefringent texture. Differential scanning calorimetry is completed using portions (60 and 60 milligrams) of the cured casting and a heating rate of 10 deg. C. per minute under a stream of nitrogen flowing at 35 cubic centimeters per minute and a temperature range from 30 to 300 deg. C. A glass transition temperature of 155.8 deg. C. and no residual cure energy are observed (average of two samples).

EXAMPLE 11

Preparation of a Casting from 4,4'-Diglycidyloxy-alpha-methylstilbene Cured with 4,4'-bis(2-Aminophenoxy)-alpha-methylstilbene and Determination of Flexural Properties A portion (14.49 grams, 0.1402 —NH equivalent) of 4,4'bis(4-aminophenoxy)-alpha-methylstilbene prepared using the method of Example 7-B (second synthesis) (103.357 —NH equivalent weight) and a portion (25.03 grams, 0.1402 epoxide equivalent) of 4,4'- diglycidyloxy-alpha-methylstilbene from Example 2-A are placed in ovens preheated to 130 and 150 deg. C., respectively. After melts are achieved, the two components are combined and stirred for the next 4.5 minutes, followed by degassing for 1.5 minutes in a vacuum bell jar. After degassing, the resin is poured into a glass mold (5 inch by 4 inch by 0.125 inch) preheated to 130 deg. C. After 4 hours at 130 deg. C., the temperature of the oven is increased to 140 deg. C. After one hour at 140 deg. C., the temperature in the oven is increased by 20 deg. C. every hour. After 200 deg. C. is achieved, the temperature in the oven is maintained therein for the next 2 hours. After cooling the oven, the recovered casting is translucent and possesses a high level of birefringence when viewed by microscopy under crosspolarized light at 70X magnification. Differential scanning calorimetry is completed using portions (80 and 40 milligrams) of the cured casting and a heating rate of 10 deg. C. per minute under a stream of nitrogen flowing at 35 cubic centimeters per minute and a temperature range from 30 to 300 deg. C. A glass transition temperature of 165.5 deg. C. and no residual cure energy are observed (average of two samples). A series of five test pieces are cut from the casting for testing of flexural properties using standard methods (ASTM D 790-86). The average flexural strength thus obtained is 14,982 psi and the average flexural modulus is 443,100 psi. All of the test pieces yielded without breaking (percent strain >15).

EXAMPLE 12

Dynamic Mechanical Analysis of a Casting from 4,4'-Diglycidyloxy-alpha-methylstilbene Cured with 4,4'-bis(2-Aminophenoxy)-alpha-methylstilbene A portion (31.73 by 6.09 by 3.19 mm) of the casting from Example 11 is subjected to dynamic mechanical analysis in the resonant mode using standard methods (ASTM D 4065-82). A 5 deg. C. per minute rate of heatup is employed with a temperature range of 30 to 250 deg. C. Storage modulus (E') values thus determined are as follows for selected temperatures. The maximum temperature observed for the tan delta transition is 196.3 deg. C.

| Temperature (deg. C.) | Storage Modulus (GPa) |
|---|---|
| 30 | 2.933 |
| 93 | 2.151 |
| 121 | 1.735 |
| 149 | 1.272 |
| 177 | 0.5183 |
| 204 | 0.0751 |
| 232 | 0.0279 |

EXAMPLE 13

Single Edge Notch Three Point Bend Testing of a Casting from 4,4'-Diglycidyloxy-alpha-methylstilbene Cured with 4,4,-bis(2-Aminophenoxy)-alpha-methylstilbene A portion (50.02 grams, 0.4814 —NH equivalent) of 4,4'-bis(2-aminophenoxy)-alpha-methylstilbene prepared using the method of Example 7-B (second synthesis) (103.916 —NH equivalent weight) and a portion (85.95 grams, 0.4814 epoxide equivalent) of 4,4'-diglycidyloxy-alpha-methylstilbene from Example 2-A are placed in ovens preheated to 130 and 150 deg. C., respectively. After melts are achieved, the two components are combined are combined and stirred for the next 2.5 minutes, followed by degassing for 30 seconds in a vacuum bell jar. After degassing, the resin is poured into a glass mold (6 inch by 5 inch by 0.250 inch) preheated to 130 deg. C. After 4 hours at 130 deg. C., the temperature of the oven is increased to 140 deg. C. After one hour at 140 deg. C., the temperature in the oven is increased 160 deg. C. After one hour at 160 deg. C., the temperature in the oven is increased 180 deg. C. After one hour at 180 deg. C., the temperature in the oven is increased 200 deg. C. After 200 deg. C. is achieved, the temperature in the oven is maintained therein for the next 2 hours. After cooling the oven, the recovered casting is translucent and possesses a high level of birefringence when viewed by microscopy under crosspolarized light at 70X magnification. Differential scanning calorimetry is completed using portions (80 and 80 milligrams) of the cured casting and a heating rate of 10 deg. C. per minute under a stream of nitrogen flowing at 35 cubic centimeters per minute and a temperature range from 30 to 300 deg. C. A glass transition temperature of 153.5 deg. C. and no residual cure energy are observed (average of two samples). A series of eleven test pieces are cut from the casting for single edge notch three point bend testing using standard methods (ASTM E 399-83). The average $G_{Ic}$ thus obtained is 702 joules / m$^2$ and the average $K_{Ic}$ is 1.57 MPa $\cdot$m$^{0.5}$.

EXAMPLE 14

Preparation of a Casting from 4,4'-Diglycidyloxy-alpha-methylstilbene Cured with 4,4'-bis(2-Aminophenoxy)-alpha-methylstilbene and Determination of Tensile Properties A portion (35.92 grams. 0..3389 —NH equivalent) of 4,4'bis(4-aminophenoxy)-alpha-methylstilbene prepared using the method of Example 7-B (second synthesis) (105.98 —NH equivalent weight) and a portion (60.25 grams, 0.3389 epoxide equivalent) of 4,4'-diglycidyloxy-alpha-methylstilbene from Example 2-A are placed in ovens preheated to 130 and 150 deg. C., respectively. After melts are achieved, the two components are combined and stirred for the next 3 minutes, followed by degassing for 30 seconds in a vacuum bell jar. After degassing, the resin is poured into a glass mold (7.5 inch by 6 inch by 0.125 inch) preheated to 130 deg. C. After 4 hours at 130 deg. C., the temperature of the oven is increased to 140 deg. C. After one hour at 140 deg. C., the temperature in the oven is increased to 160 deg. C. After one hour at 160 deg. C., the temperature in the oven is increased to 180 deg. C. After one hour at 180 deg. C., the temperature in the oven is increased to 200 deg. C. After 200 deg. C. is achieved, the temperature in the oven is maintained therein for the next 2 hours. After cooling the oven, the recovered casting is translucent and possesses a high level of birefringence when viewed by microscopy under crosspolarized light at 70X magnification. Differential scanning calorimetry is completed using portions (40 and 40 milligrams) of the cured casting and a heating rate of 10 deg. C. per minute under a stream of nitrogen flowing at 35 cubic centimeters per minute and a temperature range from 30 to 300 deg. C. A glass transition temperature of 154.8 deg. C. and no residual cure energy are observed (average of two samples). A series of six Type I test pieces are cut from the casting for testing of tensile properties using standard methods (ASTM D 638-89) (strain rate =0.2 inch / minute). The average tensile strength thus obtained is 11,400 psi (±89 psi), the average tensile modulus is 429,000 psi (±23,000 psi) and the elongation to break is 11.2 % (±0.6 %).

EXAMPLE 15

Preparation and Copolymerization of a Curable Blend of 4,4'-bis(2-Aminophenoxy)-alpha-methylstilbene, 4,4'bis(4-Aminophenoxy)-alpha-methylstilbene and 4,4'-Diglycidyloxy-alpha-methylstilbene at a 1:1 Weight Ratio A portion (3.4422 grams, 0.01928 epoxide equivalents) of 4,4'-diglycidyloxy-alpha-methylstilbene from Example 2-A is placed in an oven preheated to 150 deg. C. After a melt is achieved, 4,4'bis(2-aminophenoxy)-alpha-methylstilbene (1.0000 grams, 0.00948 —NH equivalent) and 4,4'-bis(4-aminophenoxy)-alpha-methylstilbene (1.0000 grams, 0.00979 —NH equivalent) are combined with the molten epoxy resin and stirred every 2-3 minutes, while maintained in a 130 deg. C. oven. After 6 minutes, the resin is a homogeneous solution. After an additional 4 minutes, the blend is added to an aluminum dish held in the 130 deg. C. oven. One minute later, a sample of the blend is removed for analysis. Analysis via microscopy under crosspolarized light is completed using a microscope equipped with a programmable hot stage using a heating (cooling) rate of 10 deg. C. per minute and 70X magnification. The following results are obtained: at 130 deg. C., the blend is a translucent melt containing a trace of crystals; at 72 deg. C., additional crystals form, but the overall amount is still minor; at 54 deg. C. the amount of crystals continues to increase; at 48 deg. C., a liquid crystal phase starts to form; at 46 deg. C., shear is applied by moving the coverslip over the slide, resulting in opalescence and the formation of small needlelike domains which are oriented perpendicular to the direction that the shear is applied. Nine minutes after the initial sample of the blend is taken for analysis, a second sample is taken and analyzed via microscopy under crosspolarized light using the aforementioned conditions. The following results are obtained: at 130 deg. C., the blend is a viscous, translucent melt free of crystals; at 80.7 deg. C., a liquid crystal phase starts to form; at 75 deg. C., shear is applied by moving the coverslip over the slide, resulting in smectic textures being observed 5 minutes after the sample is sheared and held at the 75 deg. C. temperature. Orientation of the fiberlike domains is observed perpendicular to the direction that the shear is applied. Fifteen minutes after the initial sample of the blend is taken for analysis, a third sample (opaque, tack free solid when cooled to room temperature) is taken and analyzed via microscopy under crosspolarized light using the aforementioned conditions. The following results are obtained: at 130 deg. C., the blend is a viscous, translucent melt free of crystals; at 110 deg. C., a liquid crystal phase forms; at 100 deg. C., shear is applied by moving the coverslip over the slide, resulting in orientation of the liquid crystalline birefringent striations in the direction (parallel) that the shear is applied. This same morphology is observed 5 minutes after the sample is sheared and held at the 100 deg. C. temperature. Twenty minutes after the initial sample of the blend is taken for analysis, the blend is a translucent gel which becomes an opaque solid at room temperature with liquid crystal textures observed via microscopy under crosspolarized light.

EXAMPLE 16

Preparation and Copolymerization of a Curable Blend of 4,4'-bis(2-Aminophenoxy)-alpha-methylstilbene, 4,4'-bis(4-Aminophenoxy)-alpha-methylstilbene and 4,4'-Diglycidyloxy-alpha-methylstilbene at a 2:1 Weight Ratio A portion (3.8517 grams, 0.02157 epoxide equivalents) of 4,4'-diglycidyloxy-alpha-methylstilbene from Example 2-A is placed in an oven preheated to 150 deg. C. After a melt is achieved, 4,4'bis(2-aminophenoxy)-alpha-methylstilbene (1.500 grams, 0.01422 —NH equivalent) and 4,4'-bis(4-aminophenoxy)-alpha-methylstilbene (0.7500 grams, 0.00735 —NH equivalent) are combined with the molten epoxy resin and stirred every 2-3 minutes, while maintained in a 130 deg. C. oven. After 7 minutes, the resin is a homogeneous solution. After an additional 3 minutes, the blend is added to an aluminum dish held in the 130 deg. C. oven. One minute later, a sample of the blend is removed for analysis. Analysis via microscopy under crosspolarized light is completed using a microscope equipped with a programmable hot stage using a heating (cooling) rate of 10 deg. C. per minute and 70X magnification. The following results are obtained: at 130 deg. C., the blend is a translucent melt containing a trace of crystals; at 42 deg. C., additional crystals form, but the overall amount is still minor; at 37 deg. C., a liquid crystal phase starts to form; at 35 deg. C., shear is applied by moving the coverslip over the slide, resulting in the formation of liquid crystalline birefringent striations oriented in the direction (parallel) that the shear is applied. Nine minutes after the initial sample of the blend is taken for analysis, a second sample is taken and analyzed via microscopy under crosspolarized light using the aforementioned conditions. The following results are obtained: at 130 deg. C., the blend is a viscous, translucent melt containing a trace of crystals; at 60 deg. C., a liquid crystal phase starts to form; at 55 deg. C., shear is applied by moving the coverslip over the slide, resulting in the formation of liquid crystalline birefringent striations oriented in the direction (parallel) that the shear is applied being observed and birefringent needlelike domains 5 minutes after the sample is sheared and held at the 55 deg. C. temperature. Orientation of these needlelike domains is observed perpendicular to the direction that the shear is applied. Fourteen minutes after the initial sample of the blend is taken for analysis, a third sample (opaque, rubbery solid when cooled to room temperature) is taken and analyzed via microscopy under crosspolarized light using the aforementioned conditions. The following results are obtained: at 130 deg. C., the blend is a viscous, translucent melt free of crystals; at 75 deg. C., a liquid crystal phase forms; at 70 deg. C., shear is applied by moving the coverslip over the slide, resulting in the formation of liquid crystalline birefringent striations oriented in the direction (parallel) that the shear is applied being observed and birefringent needlelike domains 5 minutes after the sample is sheared and held at the 70 deg. C. temperature. Orientation of these needlelike domains is observed perpendicular to the direction that the shear is applied, but is not as pronounced as that observed for the previous sample. Nineteen minutes after the initial sample of the blend is taken for analysis, a fourth sample (partially opaque solid when cooled to room temperature) is taken and analyzed via microscopy under crosspolarized light using the aforementioned conditions. The following results are obtained: at 130 deg. C., the blend is a viscous, translucent melt free of crystals; at 86 deg. C., a liquid crystal phase forms; at 80 deg. C., shear is applied to the barely mobile blend by moving the coverslip over the slide, resulting in the formation of liquid crystalline birefringent striations oriented in the direction (parallel) that the shear is applied being observed. Five minutes after the sample is sheared and held at the 80 deg. C. temperature, liquid crystalline birefringent striations oriented in the direction (parallel) that the shear is applied are still observed. Twenty nine minutes after the initial sample of the blend is taken for analysis, the blend is a translucent rubbery gel which becomes a partially opaque solid at room temperature with birefringence but no domain structures observed via microscopy under crosspolarized light.

EXAMPLE 17

Injection Molding of a Curable Blend of 4,4'-bis(2-Aminophenoxy)-alpha-methylstilbene, 4,4'-bis(4-Aminophenoxy)-alpha-methylstilbene and 4,4'Diglycidyloxy-alpha-methylstilbene at a 1:1 weight Ratio and Determination of the Flexural Properties of the Injection Molded Casting A portion (5.1633 grams, 0.02892 epoxide equivalents) of 4,4'-diglycidyloxy-alpha-methylstilbene from Example 2-A is placed in an oven preheated to 150 deg. C. After a melt is achieved, 4,4'-bis(2-aminophenoxy)-alpha-methylstilbene (1.5000 grams, 0.01423 —NH equivalent) and 4,4'-bis(4-aminophenoxy)-alpha-methylstilbene (1.5000 grams, 0.01469 —NH equivalent) are combined with the molten epoxy resin and stirred every 2-3 minutes, while maintained in a 130 deg. C. oven. After 7.5 minutes, the resin solution is degassed under a vacuum for 30 seconds. After an additional 75 seconds, the resin is poured into the reservoir of an injection molder preheated to 120 deg. C. After a total of 12 minutes in the reservoir, the molten resin is viscous and translucent and heating to the reservoir ceases. After an additional 4.5 minutes, the reservoir is at 100 deg. C., the resin is opaque and is injected through a 0.020 inch by 0.375 inch (0.5 by 9.5 mm) rectangular flow gate into a mold preheated to 60 deg. C. and having the following dimensions: 3.0 inches by 0.5 inch by 0.125 inch (76.2 by 12.7 by 3.125 mm). At the time of injection molding, a sample of the resin is removed from the reservoir and cooled to room temperature (24 deg. C.). A portion of this sample removed before cooling is placed on a stage preheated to 120 deg. C. and examined by microscopy under crosspolarized light at 70X magnification. This microscopic examination reveals the resin to be a viscous translucent liquid with a trace of birefringent phase present having a batonnet appearance. After 15 seconds at 120 deg. C., cooling at a rate of 10 deg. C. per minute commences. At 106 deg. C., the amount of birefringent domains increase. At 100 deg. C., shearing of the resin by moving the glass coverslip over the slide produces birefringent striations in the direction that the shear is applied. At 90 deg. C., shear is again applied and produces some morphology with orientation perpendicular to the direction that the shear is applied. This combined morphology of birefringent striations both parallel and perpendicular to the direction that the shear is applied is maintained at 60 deg. C. at which point the resin solidifies. A second portion of this sample is placed on a stage and examined by microscopy under crosspolarized light at 70X magnification while heating at 10 deg. C. per minute. At 30 deg. C., the resin is an opaque solid. At 112 deg. C., dispersed birefringent domains are observed. At 132 deg. C., some clearing of the birefringent phase is observed. At 180 deg. C., the opaque resin containing birefringent domains thermosets. This same morphology is maintained upon cooling to room temperature (24 deg. C.). Portions (19.1 and 20.1 milligrams) of the sample removed from the reservoir at the time of injection molding are analyzed by differential scanning calorimetry using a heating rate of 10 deg. C. per minute under a stream of nitrogen flowing at 35 cubic centimeters per minute and a temperature range from 30 to 300 deg. C. An exotherm is obtained with a maximum at 168.7 deg. C. and an enthalpy of 185.4 joules per gram (average of two samples). The mold is removed from the injection molder immediately after completion of the resin injection then placed in an oven preheated to 60 deg. C. After one hour at 60 deg. C., the temperature in the oven is increased by 10 deg. C. every hour until a temperature of 120 deg. C. is achieved. After one hour at 120 deg. C., the temperature in the oven is increased by 20 deg. C. every hour until 180 deg. C. is achieved. After 180 deg. C. is achieved, the temperature in the oven is maintained therein for the next 4 hours. After cooling the oven, the recovered casting is opaque with flow patterns on its surface and possesses birefringent domains when viewed by microscopy under crosspolarized light at 70X magnification. The flashing around the edges of the casting exhibits birefringent liquid crystal domains oriented perpendicular to the shear direction. Differential scanning calorimetry is completed using portions (60 and 60 millgrams) of the cured casting and a heating rate of 10 deg. C. per minute under a stream of nitrogen flowing at 35 cubic centimeters per minute and a temperature range from 30 to 300 deg. C. A glass transition temperature of 157.7 deg. C. and no residual cure energy are observed (average of two samples). The casting is tested for flexural properties using standard methods (ASTM D 790-86). The average flexural strength thus obtained is 17,266 psi and the average flexural modulus is 554,600 psi.

What is claimed is:

1. A curable composition comprising (A) a curing amount or more bis(aminophenoxy)-alpha-substituted stilbenes represented by the following Formula I

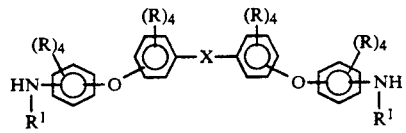

wherein each R is independently hydrogen or a hydrocarbyl or hydrocarbyloxy group having from one to about 10 carbon atoms, a halogen atom, a nitro group, a nitrile group or a —CO—$R^2$ group; each $R^1$ is independently hydrogen or a hydrocarbyl group having from one to about 10 carbon atoms; X is a

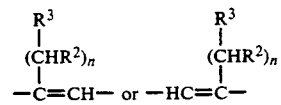

group, each $R^2$ is independently hydrogen or a hydrocarbyl group having from one to about 10 carbon atoms; $R^3$ is a hydrocarbyl group having from one to about 10 carbon atoms and may be chlorine or a nitrile group when n has a value of zero; and n has a value of zero or one; and (B) one or more epoxy resins.

2. A curable composition of claim 1 wherein in component (A) when R is a hydrocarbyl or hydrocarbyloxy group, it has from one to about 4 carbon atoms and when it is a halogen atom, it is chlorine, bromine or fluorine; when $R^1$ is a hydrocarbyl group, it has from one to about 6 carbon atoms; when $R^2$ is a hydrocarbyl group, it has from one to about 2 carbon atoms; and when $R^3$ is a hydrocarbyl group, it has from one to about 2 atoms; and component (B) is an epoxy resin represented by one of the following Formulas III, IV, V, VI, VII, VIII, IX, X, XI or mixtures thereof.

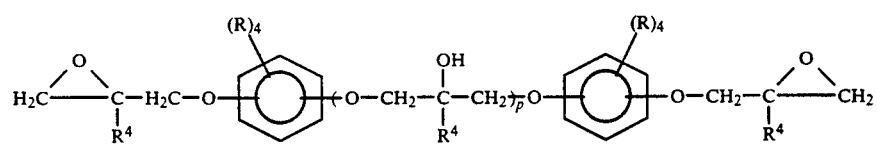
Formula III
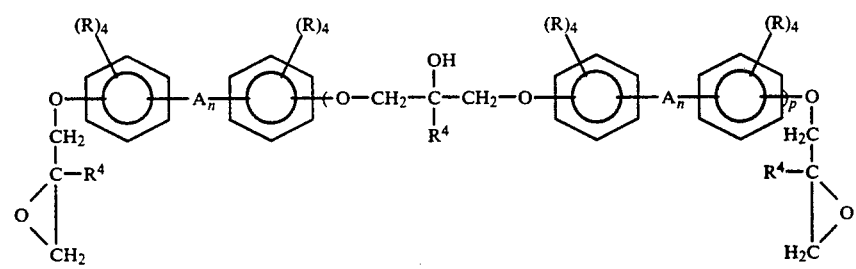
Formula IV
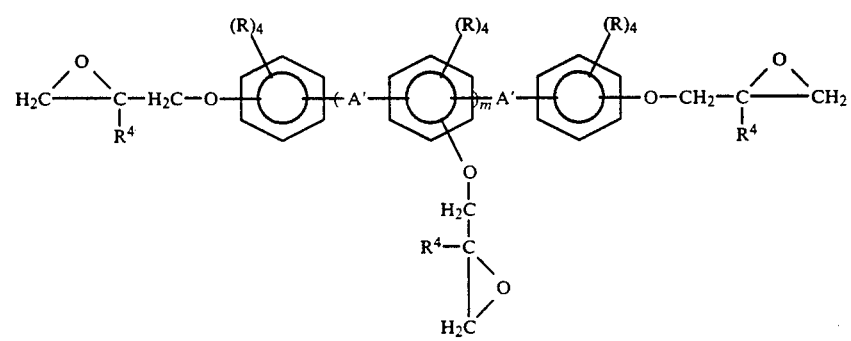
Formula V
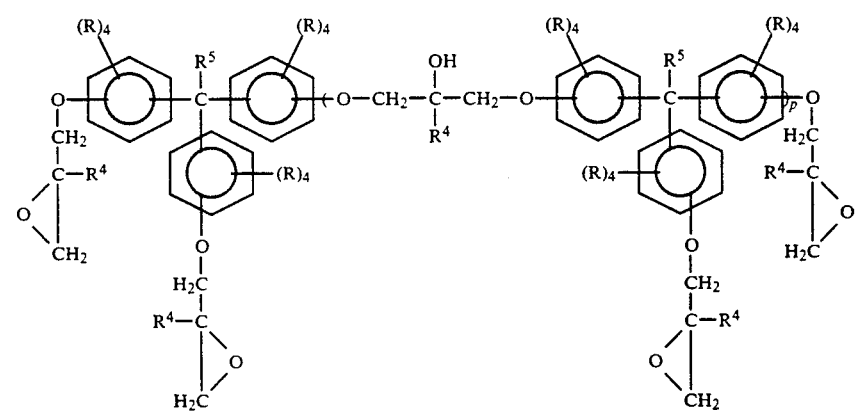
Formula VI
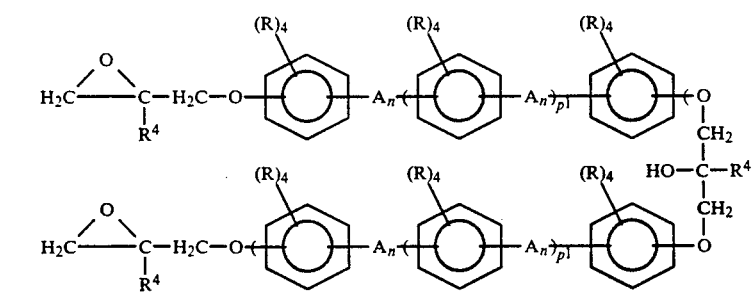
Formula VII
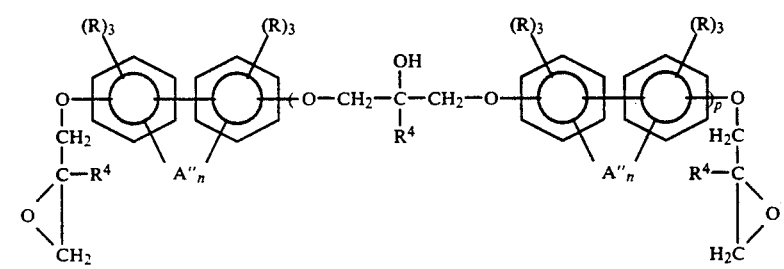
Formula VIII Formula IX

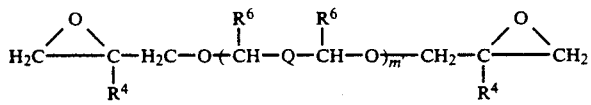

Formula X

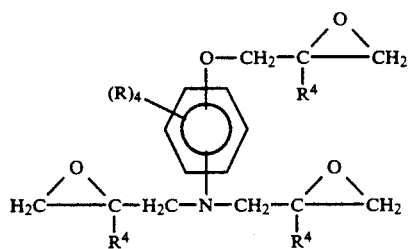

Formula XI

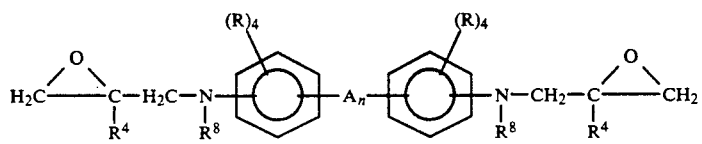

wherein each R is independently hydrogen or a hydrocarbyl or hydrocarbyloxy group having from one to about 10 carbon atoms, a halogen atom, a nitro group, a nitrile group, or a —CO—$R^2$ group; each $R^2$ is independently hydrogen or a hydrocarbyl group having from one to about 10 carbon atoms; n has a value of zero or one; each A is independently a direct single bond, a divalent hydrocarbyl group having from one to about 20 carbon atoms, —O—, —CO—, —SO—, —$SO_2$—, —S—, —S—S—, —$CR^7$=$CR^7$—, —C≡C—, —N=N—, —$CR^7$=N—, —N=$CR^7$—, —O—CO—, —CO—O—, —S—CO—, —CO—S—, —$NR^7$—CO—, —CO—$NR^7$—, —$CR^7$=N—N=$CR^7$—, —CO—$CR^7$=$CR^7$—, —$CR^7$=$CR^7$—CO—, —CO—O—N=$CR^7$—, —$CR^7$=N—O—OC—, —CO—O—N=$CR^7$—, —CO—$NR^7$—$NR^7$—OC—, —$CR^7$=$CR^7$—O—OC—, —CO—O—$CR^7$=$CR^7$—, —O —CO—$CR^7$=$CR^7$—, —$CR^7$=$CR^7$—CO—O—, —(CHR$^7$)$_n'$—O—CO—$CR^7$=$CR^7$—, —$CR^7$=C-$R^7$—CO—O—(CHR$^7$)$_n'$—, —(CHR$^7$)-$_n'$—CO—O—$CR^7$=$CR^7$—, —$CR^7$=C-$R^7$—O—CO—(CHR$^7$)$_n'$—, —$CH_2$—$CH_2$—CO—O—, —O—OC—$CH_2$—$CH_2$—, —C≡C—C≡C—, —$CR^7$=$CR^7$—$CR^7$=$CR^7$—, —$CR^7$=$CR^7$—C≡C—, —C≡C—$CR^7$=$CR^7$—, —$CR^7$=$CR^7$—CH-$_2$—O—OC—, —CO—O—$CH_2$—$CR^7$=$CR^7$—, —O—CO—C≡C—CO—O—, —O—CO—$CR^7$=C-$R^7$—CO—O—, —O—CO—$CH_2$—$CH_2$—CO—O—, —S—CO—$CR^7$=CR $^7$—CO—S—, —CO—$CH_2$—N-H—CO—, —CO—NH—$CH_2$—CO—, —NH—C-(—$CH_3$)=CH—CO—, —CO—CH=C(—CH-$_3$)—NH—, —$CR^7$=C(—Cl)—, —C(—Cl)=$CR^7$—, —$CR^7$=C(—CN)—, —C(—CN)=$CR^7$—, —N=C(—CN)—, —C(—CN)=N—, —$CR^7$=C(—CN-)—CO—O—, —O—CO—C(—CN)=$CR^7$—,

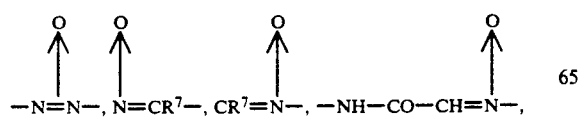

-continued

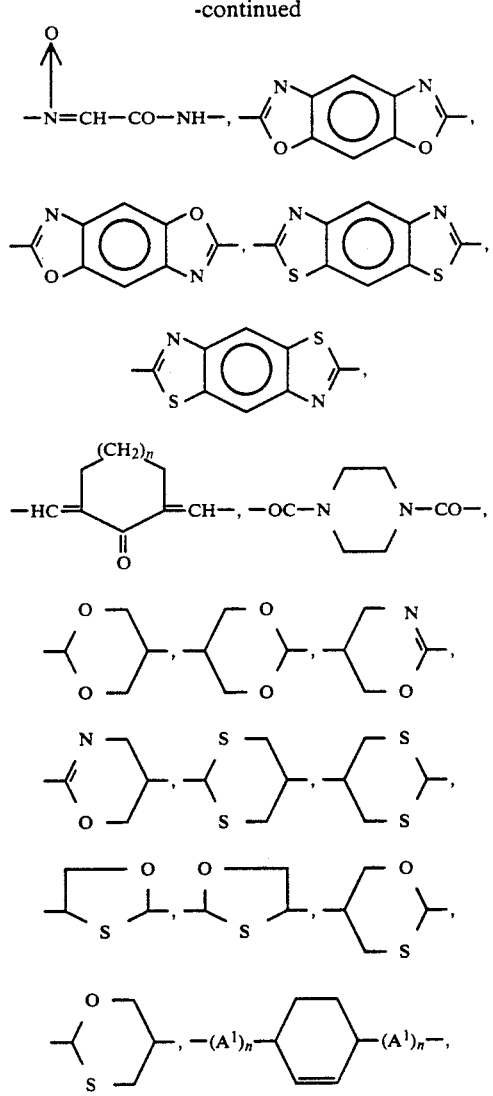

-continued

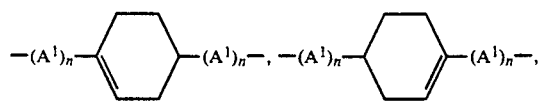

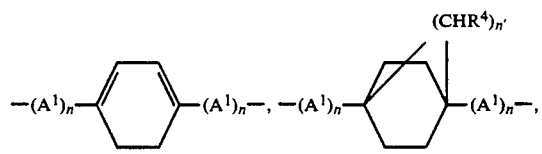

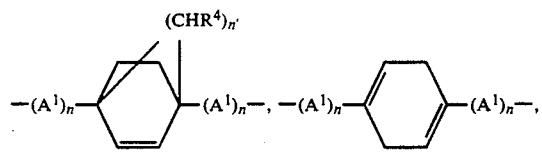

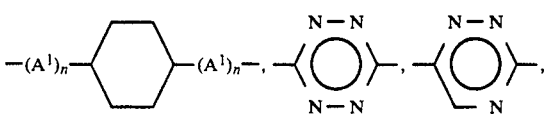

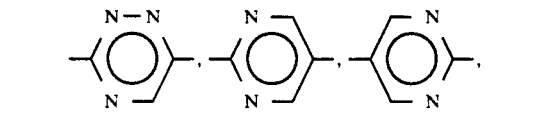

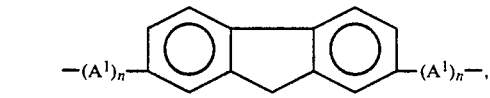

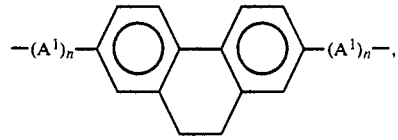

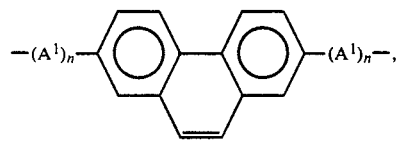

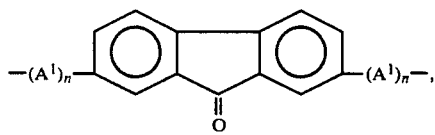

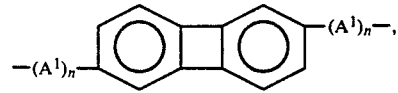

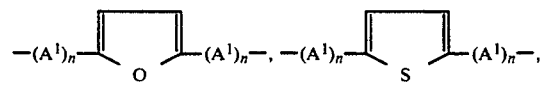

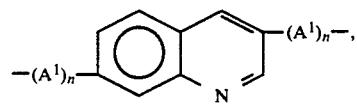

-continued

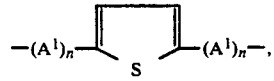

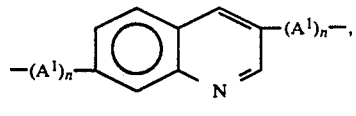

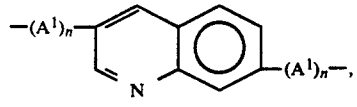

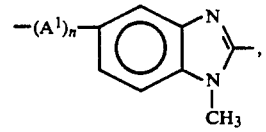

or

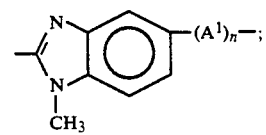

each A' is independently a divalent hydrocarbyl group having from one to about 10 carbon atoms; A" is a divalent hydrocarbyl group having from one to about 6 carbon atoms; each $A^1$ is independently a —CO—, —O—CO—, —CO—O—, —CO—S—, —S—CO—, —CO—NR$^7$— or —NR$^7$—CO—; each $R^4$ is independently hydrogen or a hydrocarbyl group having from one to about 3 carbon atoms; each $R^5$ is independently hydrogen, a hydrocarbyl group having from one to about 10 carbon atoms or a halogen atom; each $R^6$ is independently hydrogen or a hydrocarbyl or halohydrocarbyl group having from one to about 6 carbon atoms; Q is a direct bond, —CH$_2$—S—CH$_2$—, —(CH$_2$)$_n$"—, or

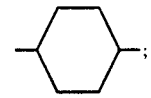

each $R^7$ is independently hydrogen or a hydrocarbyl group having from one to about 6 carbon atoms; each $R^6$ is independently a hydrocarbyl group having from 1 to about 10 carbon atoms or a

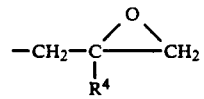

group; m has a value from about 0.001 to about 6; m' has a value from one to about 10; n' has a value of one or two, n" has an average value of from about one to about 10; p has a value from zero to about 30 and p$^1$ has a value of from one to about 30; wherein the aromatic rings can optionally contain one or more heteroatoms selected from N, O or S; and the A" hydrocarbyl group of Formula VIII can also optionally include one or more heteroatoms selected from N, O or S.

3. A curable composition of claim 2 wherein component (A) is a 4,4'-bis(aminophenoxy)-alpha-alkylstilbene or a N,N'-dialkyl-4,4'-bis(aminophenoxy)-alpha-alkylstilbene and component (B) is a mesogenic epoxy resin represented by one of the following Formulas IV, VII, VIII or XI or mixtures thereof.

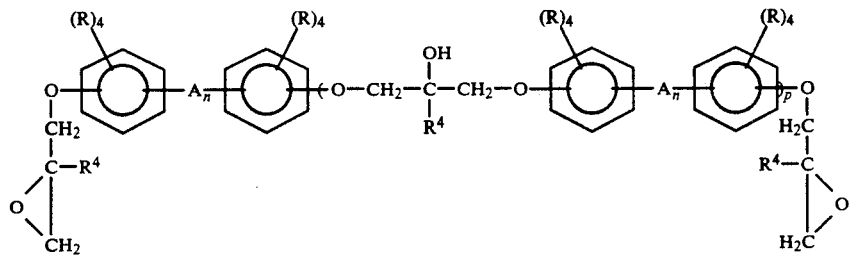

Formula IV

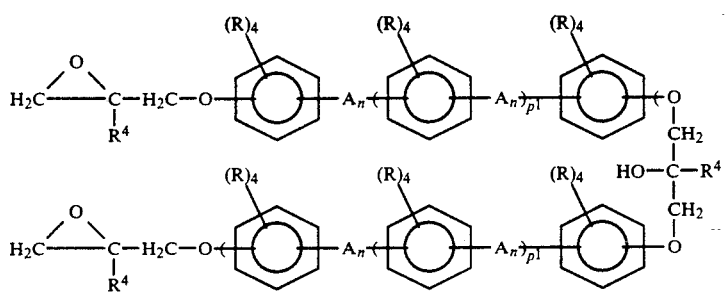

Formula VII

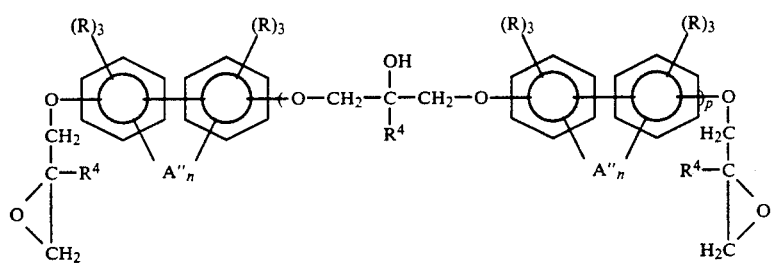

Formula VIII

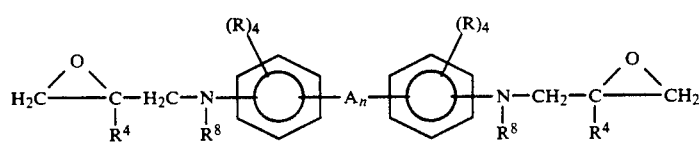

Formula XI wherein each R is independently hydrogen or a hydrocarbyl or hydrocarbyloxy group having from one to about 10 carbon atoms, a halogen atom, a nitro group, a nitrile group, or a —CO—R$^2$ group; each R$^2$ is independently hydrogen or a hydrocarbyl group having from one to about 10 carbon atoms; n has a value of zero or one; each A is independently a direct single bond, —CR$^7$=CR$^7$—, —C≡C—, —N=N—, —CR$^7$=N—, —N=CR$^7$—, —O—CO—, —CO—O—, —S—CO—, —CO—S—, —NR$^7$—CO—, —CO—NR$^7$—, —CR$^7$=N—N=CR$^7$—, —CO—CR$^7$=CR$^7$—, —CR$^7$=CR$^7$—CO—, —CO—O—N=CR$^7$—, —CR$^7$=N—O—OC—, —CO—O—N=CR$^7$—, —CO—NR$^7$—NR$^7$—OC—, —CR$^7$=CR$^7$—O—OC—, —CO—O—CR$^7$=CR$^7$—, —O—CO—CR$^7$=CR$^7$—, —CR$^7$=CR$^7$—CO—O—, —(CHR$^7$)$_{n'}$—O—CO—CR$^7$=CR$^7$—, —CR$^7$=CR$^7$—CO—O—(CHR$^7$)$_{n'}$—, —(CHR$^7$)$_{n'}$—CO—O—CR$^7$=CR$^7$—, —CR$^7$=CR$^7$—O—CO—(CHR$^7$)$_{n'}$—, —CH$_2$—CH$_2$—CO—O—, —O—OC—CH$_2$—CH$_2$—, —C≡C—C≡C—, —CR$^7$=CR$^7$—CR$^7$=CR$^7$—, —CR$^7$=CR$^7$—C≡C—, —C≡C —CR$^7$=CR$^7$—, —CR$^7$=CR$^7$—CH$_2$—O—OC—, —CO—O—CH$_2$—CR$^7$=CR$^7$—, —O—CO—C≡C—CO—O—, —O—CO—CR$^7$=CR$^7$—CO—O—, —O—CO—CH$_2$—CH$_2$—CO—O—, —S—CO—CR$^7$=CR$^7$—, R$^7$—CO—S—, —CO—CH$_2$—NH—CO—, —CO—NH—CH$_2$—CO—, —NH—C(—CH$_3$)=CH—CO—, —CO—CH=C(—CH$_3$)—NH—, —CR$^7$=C(—Cl)—, —C(—Cl)=CR$^7$—, —CR$^7$=C(—CN)—, —C(—CN)=CR$^7$—, —N=C(—CN)—, —C(—CN)=N—, —CR$^7$=C(—CN)—CO—O—, —O—CO—C(—CN)=CR$^7$—,

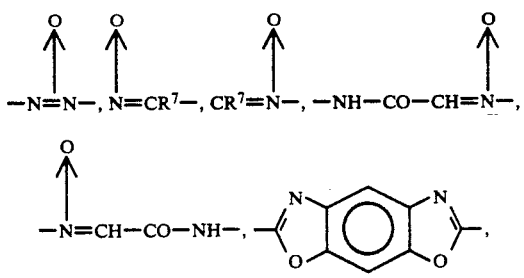

-continued

A" is a divalent hydrocarbyl group having from one to about 6 carbon atoms; each $A^1$ is independently a —CO—, —O—CO—, —CO—O—, —CO—S—, —S—CO—, —CO—$NR^7$— or —$NR^7$—CO— group; each $R^4$ is independently hydrogen or a hydrocarbyl group having from one to about 3 carbon atoms; each $R^7$ is independently hydrogen or a hydrocarbyl group having from one to about 6 carbon atoms; each $R^8$ is a hydrocarbyl group having from 1 to about 10 carbon atoms; n' has a value of one or two; p has a value from zero to about 30 and $p^1$ has a value of from one to about 30; wherein the aromatic rings can optionally contain one or more heteroatoms selected from N, O or S; and the A" hydrocarbyl group of Formula VIII can also optionally include one or more heteratoms selected from N, O or S.

4. A curable composition of claim 1 which additionally contains one or more curing agents or curing catalysts or a combination of curing agents and curing catalysts.

5. A curable composition of claim 4 wherein said curing agent is selected from aliphatic, cycloaliphatic, polycycloaliphatic or aromatic primary or secondary polyamines; carboxylic acids or anhydrides thereof; aromatic hydroxyl containing compounds; imidazoles; guanidines; urea-aldehyde resins; melamine-aldehyde resins; alkoxylated urea-aldehyde resins; alkoxylated melamine-aldehyde resins; amidoamines; epoxy resin adducts with primary or secondary amines; or any combination thereof; wherein all, none, or a part of said curing agents contain one or more mesogenic moieties.

6. The product resulting from curing a curable composition of claim 1.

7. The product resulting from curing a curable composition of claim 2.

8. The product resulting from curing a curable composition of claim 3.

9. The product resulting from curing a curable composition of claim 4.

10. The product resulting from curing a curable composition of claim 5.

11. A curable composition of claim 1, 2, 3, 4 or 5 which has been subjected to either (a) the application of an electric field or magnetic field, (b) drawing or shear forces, or (c) any combination thereof either (a) before curing or processing, (b) during curing or processing or (c) both before and during curing or processing.

12. The product resulting from curing a curable composition of claim 11.

* * * * *

UNITED STATES PATENT AND TRADEMARK OFFICE
CERTIFICATE OF CORRECTION

PATENT NO. : 5,300,594
DATED : April 5, 1994
INVENTOR(S) : V. Rao Durvasula et al.

It is certified that error appears in the above-indentified patent and that said Letters Patent is hereby corrected as shown below:

In claim 1, column 38, the formula should be --

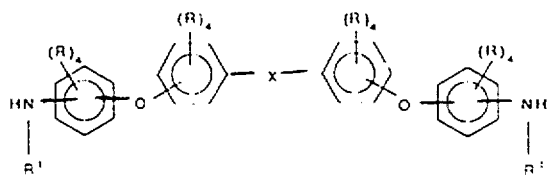

--.

In claim 2, column 44, line 54, "$R^6$" should read --$R^8$--.

Signed and Sealed this

Twenty-first Day of March, 1995

*Attest:*

BRUCE LEHMAN

*Attesting Officer*     *Commissioner of Patents and Trademarks*